United States Patent [19]

Sharon

[11] Patent Number: 5,789,208

[45] Date of Patent: Aug. 4, 1998

[54] POLYCLONAL ANTIBODY LIBRARIES

[75] Inventor: Jacqueline Sharon, Chestnut Hill, Mass.

[73] Assignee: The Trustees of Boston University, Boston, Mass.

[21] Appl. No.: 802,824

[22] Filed: Feb. 19, 1997

Related U.S. Application Data

[63] Continuation of Ser. No. 189,360, Jan. 31, 1994, abandoned.

[51] Int. Cl.$^6$ .............................. C12P 19/34; C12Q 1/68; C12N 15/13; C12N 15/64

[52] U.S. Cl. ...................... 435/91.41; 435/6; 435/6.91; 435/91.4; 435/172; 435/320.1

[58] Field of Search ........................ 435/6, 69.1, 91.4, 435/91.41, 172.3, 320.1

[56] References Cited

FOREIGN PATENT DOCUMENTS

| | | |
|---|---|---|
| 0368684A | 5/1990 | European Pat. Off. . |
| WO9014424A | 11/1990 | WIPO . |
| WO9215678 | 9/1992 | WIPO . |
| WO9218619A | 10/1992 | WIPO . |
| WO9220791A | 11/1992 | WIPO . |
| WO9303151A | 2/1993 | WIPO . |

OTHER PUBLICATIONS

Sarantopoulos, et al.: "A method for linking Vl and Vh region genes that allows bulk transer between vectors use in generating polyclonal IgG libraries", *Journal of Immunology* 152(11):5344–5351 (1994).

Manoharan, T.H. et al.; Mol. Pharmacol. 39(4):461–467, Apr. 1991.

C.F. Barbas et al., *Assembly of combinatorial antibody libraries on phage surfaces: The gene III site*, Proc. Natl. Acad. Sci. USA 88: 7878–82 (1991).

C.F. Barbas et al., *Human monoclonal Fab fragments derived from a combinatorial library bind to respiratory syncytial virus F glycoprotein and neutralize infectivity*, Proc. Natl. Acad. Sci. USA 89: 10164–68 (1992).

W.D. Huse et al., *Generation of Large Combinatorial Library of the Immunoglobulin Repertoire in Phage Lambda*, Science 246: 1275–81 (1989).

J. McCafferty et al., *Phage antibodies: filamentous phage displaying antibody variable domains*, Nature 348: 552–54 (1990).

H.R. Hogenboom et al., *Multi–subunit proteins on the surface of filamentous phage: methodologies for displaying antibody (Fab) heavy and light chains*, Nuc. Acids Res. 19: 4133–37 (1991).

M.J. Embleton et al., *In–cell PCR from a mRNA: amplifying and linking the rearranged inmmunoglobulin heavy and light chain V–genes within single cells*, Nuc. Acids Res. 20: 3831–37 (1992).

Hogrefe et al. (1993) A bacteriophage lambda vector for the cloning and expression of immumoglobulin Fab fragments on the surface of filamentious phage. Gene 128: 119–126.

Orlandi et al (1989) Cloning immunoglobulin variable domains for expression by the polymerase chain reaction. Proc. Natl. Acad. Sci. USA 86: 3833–37.

Clarkson et al (1991) Making antibody fragments using phage display libraries Nature 352: 624–628.

Swaroop et al (1988) Charon BS(+) and (–), versittle X phages vectors for constructing directional cDNA libraries and their efficient transfer to plasmids. Nucl. Acid Res. 16:8739.

*Primary Examiner*—Jasemine C. Chambers
*Assistant Examiner*—Scott D. Priebe
*Attorney, Agent, or Firm*—Ronald I. Eisenstein

[57] ABSTRACT

The invention is directed to methods for the creation and use of libraries of proteins which comprise polyclonal antibodies to a common antigen or group of antigens, receptor proteins with related variable regions, or other immune related proteins with variable regions. These polyclonal antibody libraries can be used to treat or prevent diseases and disorders including neoplasia such as cancer and other malignancies, parasitic infections, bacterial infections, viral infections and disorders such as genetic defects and deficiencies. Protein libraries may be patient-specific, disease-specific or both patient- and disease-specific. Libraries can also be used to detect a disease or disorder in a patient either by direct imaging or through the use of a diagnostic kit. The invention further includes novel cloning methods for the creation and transfer of nucleic acid sequences encoding protein variable regions and novel cloning vectors.

26 Claims, 14 Drawing Sheets

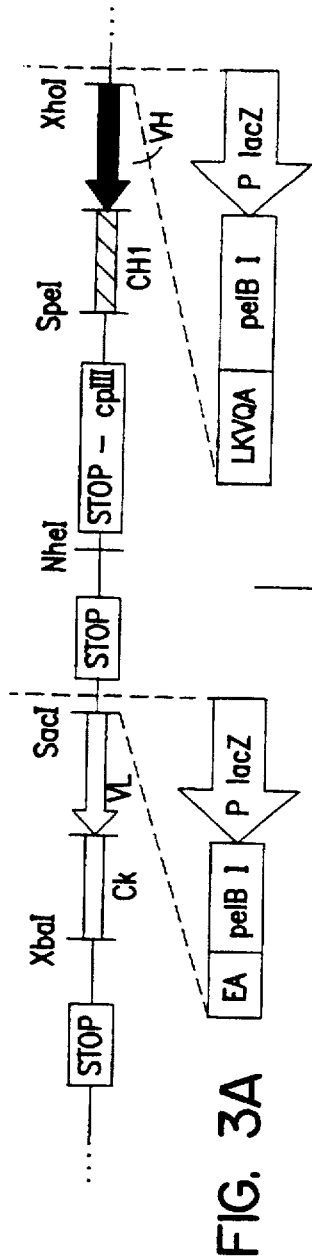
FIG. 3A
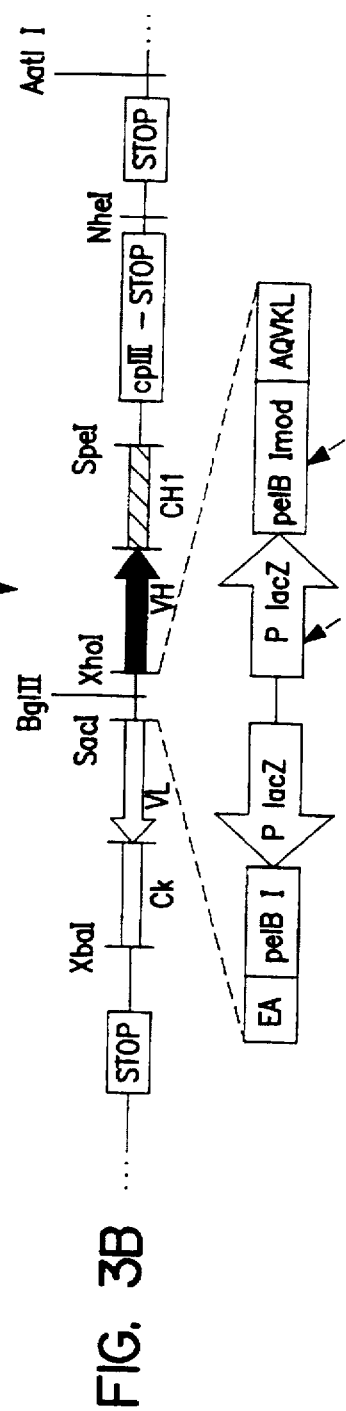
FIG. 3B
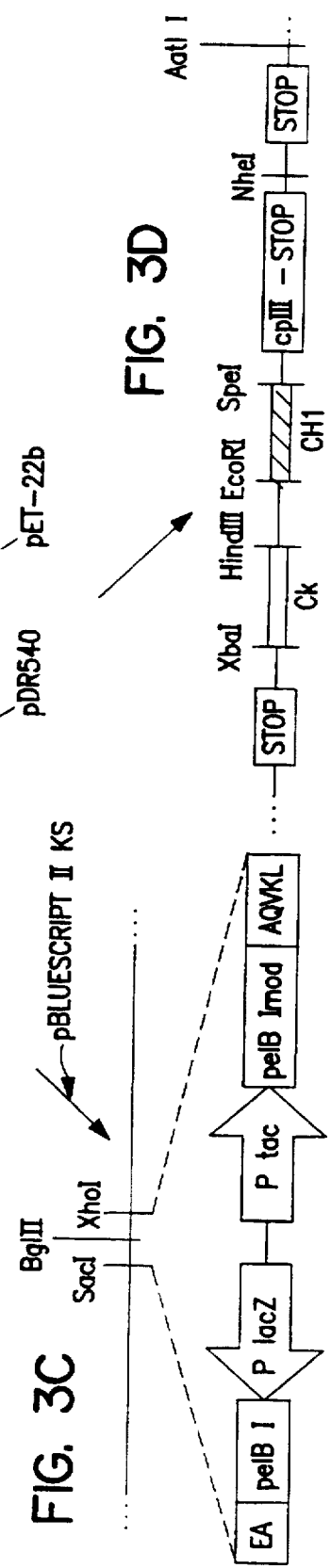
FIG. 3C
FIG. 3D

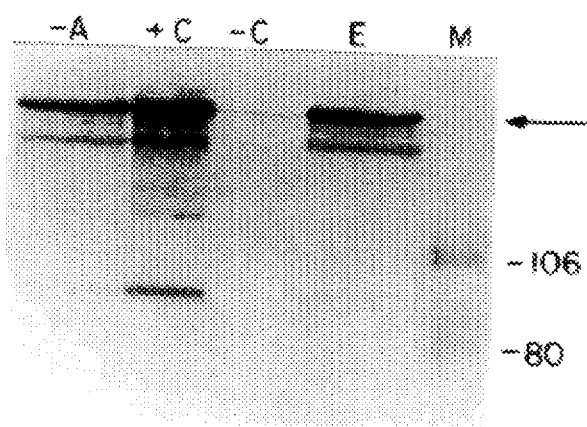
F I G. 8a
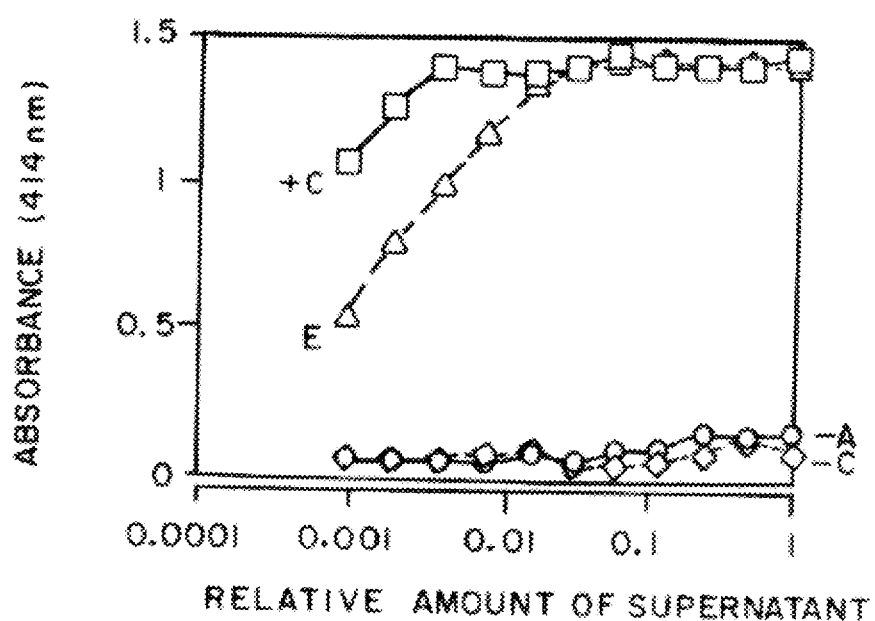
F I G. 8b

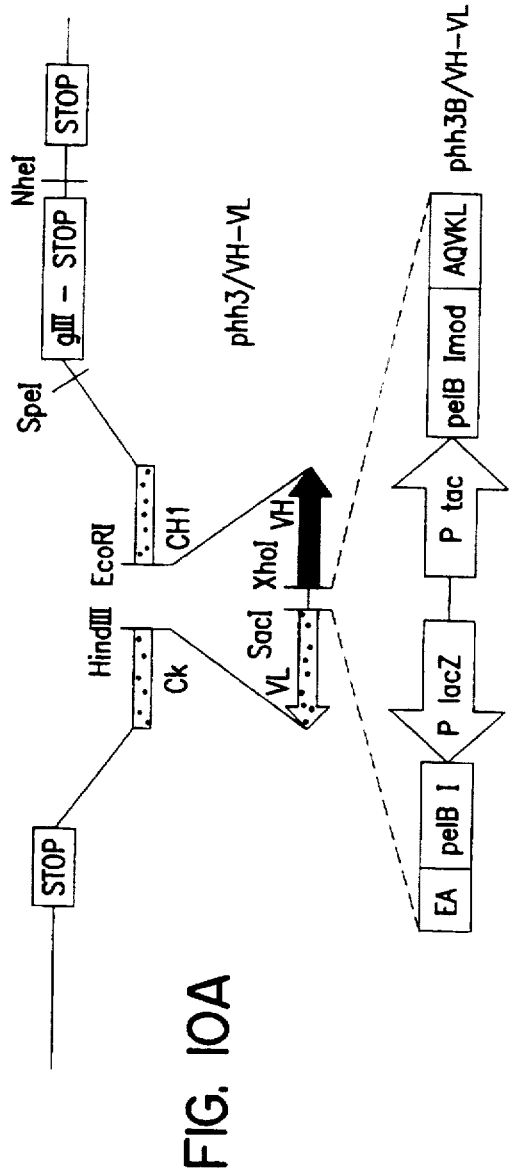
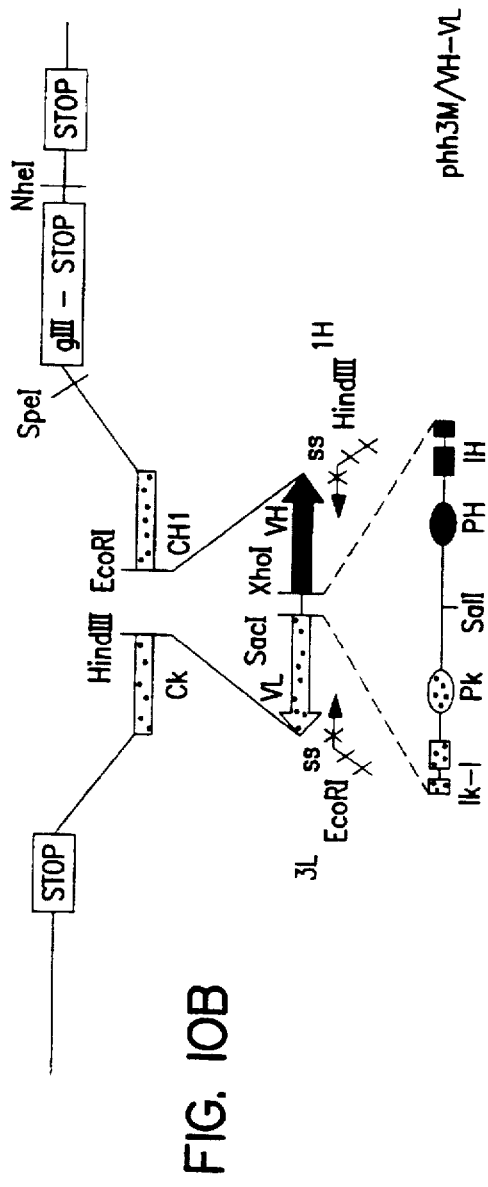
FIG. 10A
FIG. 10B

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GATGTTAACT GCTCACTGGA TGGTGGG                                                                           2 7

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:2:

CAGTTGTATC TCCACACCCA GGGGCCAG  28

( 2 ) INFORMATION FOR SEQ ID NO:3:

( i ) SEQUENCE CHARACTERISTICS:
      ( A ) LENGTH: 69 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:3:

CAGTCAGTCA GTCAGTCAGT CAGTCAGTCA GAGCTCCAGA TGACACAGAC TACATCCTCC  60

CTGTCTGCC  69

( 2 ) INFORMATION FOR SEQ ID NO:4:

( i ) SEQUENCE CHARACTERISTICS:
      ( A ) LENGTH: 71 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:4:

CTGACTGACT GACTGACTGA CTGACTGACT GAGGTTCAGC TTCTCGAGTC TGGAGCTGAG  60

CTGGTGAGGG C  71

( 2 ) INFORMATION FOR SEQ ID NO:5:

( i ) SEQUENCE CHARACTERISTICS:
      ( A ) LENGTH: 57 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:5:

GATGGATACA GTTGGGAATT CATTCTACTT ACGTTTGATT CCAGCTTGG TGCCTCC  57

( 2 ) INFORMATION FOR SEQ ID NO:6:

( i ) SEQUENCE CHARACTERISTICS:
      ( A ) LENGTH: 53 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:6:

GGATAGACTG ATGGAAGCTT GGACTCACCT GAGGAGACTG TGAGAGTGGT GCC  53

( 2 ) INFORMATION FOR SEQ ID NO:7:

( i ) SEQUENCE CHARACTERISTICS:
      ( A ) LENGTH: 24 base pairs
      ( B ) TYPE: nucleic acid
      ( C ) STRANDEDNESS: single
      ( D ) TOPOLOGY: linear -continued (i i) MOLECULE TYPE: DNA (genomic)

(x i) SEQUENCE DESCRIPTION: SEQ ID NO:7:

GCCACTGAAC CTTGATGGGA CTCC                                                              24

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:8:

GTGTCATCTG GAGCTCACAT CTGG                                                              24

(2) INFORMATION FOR SEQ ID NO:9:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:9:

CCTCACCAGC TAAGCTTCAG ATTCAGACTC GAGAAGCTGA AC                                           42

(2) INFORMATION FOR SEQ ID NO:10:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (x i) SEQUENCE DESCRIPTION: SEQ ID NO:10:

Leu  Lys  Val  Gln  Ala
 1                   5

(2) INFORMATION FOR SEQ ID NO:11:

(i) SEQUENCE CHARACTERISTICS:
        (A) LENGTH: 5 amino acids
        (B) TYPE: amino acid
        (C) STRANDEDNESS: unknown
        (D) TOPOLOGY: unknown (x i) SEQUENCE DESCRIPTION: SEQ ID NO:11:

Ala  Gln  Val  Lys  Leu
 1                   5

POLYCLONAL ANTIBODY LIBRARIES

This application is a continuation of application Ser. No. 08/189,360 filed on Jan. 31, 1994 now abandoned.

RIGHTS IN THE INVENTION

This invention was made with support from the National Institutes of Health under grant number R01/AI23909 and the United States government has certain rights in the invention.

BACKGROUND OF THE INVENTION

1. Field of the Invention

The invention relates to the creation, interconversion and use of libraries of polyclonal antibodies, cell surface receptors and other proteins with variable regions. These variable regions are linked, cloned into expression vectors which can be maintained, selected and amplified as desired, and the libraries or sub-libraries of variable regions transferred to other expression vectors without loss of overall diversity or complexity. The resulting libraries of variable regions and libraries of whole proteins can be used to treat, prevent or diagnose specific diseases and disorders including neoplasias, malignancies, infections, and genetics defects and deficiencies.

2. Description of the Background

Lymphocytes constitute about 20% of blood leukocytes and are the main components of the mammalian antigen recognition system occurring predominantly in two forms, B cells and T cells. T cells differentiate in the thymus, and possibly other tissues, into cytotoxic ($T_C$) cells, helper ($T_H$) cells and suppressor ($T_S$) cells. These T cells recognize foreign antigen in association with major histocompatibility complex (MHC) antigens via a specific T cell receptor (TcR). This receptor is highly polymorphic and clonally distributed. The typical TcR is a disulfide linked heterodimer consisting of an α and a β polypeptide which is expressed on the surface of mature T cells. The two chains are similar in size possessing a transmembrane portion encompassed within a constant region and a polymorphic variable region that possesses considerable structural homology with immunoglobulins. Each variable region is composed of a variable (V) segment, a joining (J) segment, and a diversity (D) segment (β chain only) which assemble into the polymorphic region. Such diversity is necessary for the T cells to respond to a wide variety of antigens.

B cells differentiate in the bone marrow of adult mammals developing from pre-B cells into antibody-producing plasma cells. The importance of B cells to the immune system is highlighted by those rare immunodeficiency diseases in which the patient can only survive by repeated gamma globulin injections. One of the fascinating aspects of B cells is their heterogeneity of antibody expression. It has been estimated from observations that no more than two out of every $10^8$ different antibodies could be identical. Not surprisingly, the mechanisms which are responsible for such diversity are not fully understood. Antibodies and TcRs, both having constant and variable regions, fall into what is referred to as the immunoglobulin superfamily.

The process of immunoglobulin expression is initiated with activation of resting B cells. In the T cell independent pathway, mitogen binds to surface receptors of B cells stimulating expression of fairly low affinity IgM monomers. Upon recognition of foreign antigen, these IgM monomers cross-link at the cell surface and are internalized. Antibody expression then switches to the transcription and translation of higher affinity IgG, IgE, IgA, or pentameric IgM. In the T cell dependent pathway, mitogen is again required to stimulate the resting B cell, however, after internalization, antigen is processed within the cell to reemerge on the cell surface in association with MHC class II molecules. As an antigen presenting cell (APC), antigen-MHC complexes are recognized by and stimulate T cell activation and the production of a number of T and B cell soluble mediators. Information received from these surface complexes is transmitted to the B cell's nucleus via second messengers which, among other effects, leads to increased cyclic nucleotide metabolism and protein kinase C activity. In both T cell dependent and independent pathways, B cells develop into functionally mature, antibody producing cells.

Antibodies are bifunctional molecules comprising two heavy (H) chains and two light (L) chains joined with interchain disulfide bonds. Each chain contains constant (C) and variable (V) regions, which can be broken down into domains designated $C_{H1}$, $C_{H2}$, $C_{H3}$ and $V_H$, and $C_L$ and $V_L$. IgM exists as cell surface monomers or circulating pentamers held together with a 137 amino acid peptide called the J chain. IgA molecules also circulate, but in pairs linked with J chain and contain a small secretory component (SC) which is involved in transport across epithelial membranes. Antibody binds to antigen via the variable region domains contained in the Fab portion and, after binding, interacts with the rest of the immune system through the effector functions of the constant region domain mostly through the Fc portion. Effector functions include activation of the complement cascade, interaction with effector cells such as lymphocytes, and compartmentalization of immunoglobulins. Constant regions are also thought to influence the stabilities of the different immunoglobulins. For example, IgG is relatively stable with a circulating half-life of about 23 days. IgG is also the immunoglobulin responder associated with the secondary immune response. This immunoglobulin fixes complement through the classic complement cascade and has the ability to recruit macrophages and neutrophils. Pentameric IgM is another very strong activator of the classic complement cascade and has a serum half-life of about five days. IgA has a serum half-life of 5–6 days, activates complement through the alternate pathway, and is the principal antibody in mucus secretions.

The antigen binding domains, the variable regions, are encoded in the variable region genes which are somewhat scattered in the genome and must be brought together by a process referred to as somatic recombination. In this process, the V, D and J (not related to the J chain) segments of the host genome are brought together to form a gene region. This region is spliced to the mRNA encoding the antibody's constant region domain to be expressed together as a polypeptide and ultimately as an antibody molecule.

Antibody constant regions are the principal determining features of antibody class for both heavy and light chains, and are encoded on about fifteen different genes. The five classes of heavy chain genes are designated alpha (α), gamma (γ), delta (δ), mu (μ), and epsilon (ε), and the two light chain genes, kappa (κ) and lambda (λ). Variable regions, which contain the antigen binding site, are encoded on upwards of one thousand different genetic regions. These regions selectively recombine to create the amino acid combination required to recognize and bind to the target antigen. Binding site variability is not uniformly distributed, but each domain contains a number of highly variable portions called hypervariable regions (HVR), or complementarity determining regions (CDR), and it is these regions which actually interact with antigen.

The generation of binding-site diversity is a combination of several factors: (1) the combination of different $V_H$ and $V_L$ domains, (2) the combination of different V, D, and J regions to form the variable domain, (3) the generation of novel diversity at domain junctions referred to as junctional-diversity, and (4) diversity due to somatic mutation. Somatic mutation, to a large extent, is also responsible for maturation of the immune response wherein B cell clones which proliferate during development of the humoral response have an increasingly higher affinity for the antigen. The combination of these processes, in theory, allows an organism to generate a specific immune response to nearly any antigen.

The stimulation of an antibody response is the basis behind most forms of vaccine therapy and prophylaxis. As a prophylaxis, antigen in the form of killed or attenuated microorganism or purified protein is administered to a patient. Administration of this vaccine, it is hoped, will prime the patient's immune system for the possible later recognition of that same antigen in the form of an infection. If the infection can be caught early, in other words, if anti-antigen antibodies are circulating throughout the body upon initial or early exposure to the organism, the organism may be eliminated from the body before having a chance to take hold or produce a full-blown infection. This aspect has been recognized for a very long time, even before the basic structure of the antibody was appreciated. Antibody treatments involve passive vaccinations of pooled serum in the form of gamma globulin. Blood plasma is collected from convalescent individuals or animals, who recovered from the particular disease, and refined into the proteinaceous or gamma globulin fraction, so named because it contains predominantly IgG molecules. Injections of this gamma globulin are administered many times over a period of hours or days, usually immediately after exposure to the infectious organism or toxic substance, to provide the patient with short-term protection from the infection. For example, individuals bitten by an animal suspected of harboring the rabies virus, a rhabdovirus, are administered a regiment of gamma globulin treatments to prevent the virus from infecting because once an infection takes hold the outcome is inevitably quite poor. However, if treatments are begun early the prognosis can be fairly optimistic.

The use of antibodies for cancer therapy (or prophylaxis) is based on the premise that the antigenic profile of a cancer cell is different from that of normal cells. As depicted schematically in FIG. 1, these differences could potentially include (1) antigenic determinants that are present exclusively on the surface of tumor cells, (2) intracellular molecules found exclusively in tumor cells that are presented as peptides on the cell surface in association with MHC molecules, (3) antigens that are present only on some normal cells, and (4) quantitative differences in the amount of expression of certain antigens on the surface of the tumor cells when compared with other non-tumor cell types. This premise has been substantiated by the discovery of so-called tumor-associated antigens which are not expressed in significant or measurable amounts on the surfaces of normal cells (M. Herlyn and H. Koprowski, Ann. Rev. Immunol. 6:283–308, 1988). These tumor-specific peptides are presented on the cell surface in association with class I MHC antigens.

Monoclonal antibodies, unlike polyclonal antibodies, comprise a collection of identical molecules produced by a common B cell clone which are directed against a single antigenic determinant. Monoclonal antibodies can be distinguished from polyclonal antibodies in that monoclonal antibodies must be individually selected whereas polyclonal antibodies are selected in groups of more than one or, in other words, in bulk. Large amounts of monoclonal antibodies can be produced by immortalization of a polyclonal B cell population using hybridoma technology. Each immortalized B cell can divide, presumably indefinitely, and gives rise to a clonal population of cells that each expresses an identical antibody molecule. The individual immortalized B cell clones, the hybridomas, are segregated and cultured separately.

Monoclonal antibody therapy has been increasingly used in cancer therapy and diagnosis, but suffers from several limitations. (H. Thomas and K. Sikora, Rev. Oncol. 4:107–120, 1991). Tumor cell variants, lacking the single antigenic determinant recognized by the monoclonal antibody often arise which escape treatment. Because each monoclonal antibody is directed to a single antigenic determinant on the targeted cancer cell, the density of that determinant on the cell surface is usually not high enough to allow for destruction of the cell. Further, the effector mechanisms mediated by the Fc regions of the bound antibody molecules, such as complement binding and concomitant production of C3b, opsonization/phagocytosis, and antibody-dependent, cell-mediated cytotoxicity (ADCC), are not activated. Only at high antibody densities is complement activated, or enough Fc receptors engaged, so that effector cells are triggered to perform their preordained functions. Consequently, anti-tumor monoclonal antibodies are usually ineffective for complete elimination of the target cells.

In an effort to circumvent some of these problems, methods have been developed to try and bolster the killing efficiency of monoclonal antibodies with radioactive isotopes, toxins or drugs. However, these tags can in turn cause deleterious side effects (T. A. Waldmann, Sci. 252:1657–62, 1991). Even if a monoclonal antibody (tagged or untagged) is reasonably effective at eliminating cancer cells, and remissions have been documented, in most cases the cancer relapses because tumor cell variants which have lost the target antigenic determinant escape and proliferate (R. A. Miller et al., N. Engl. J. Med. 306:517–22, 1982). This problem might be partially overcome with the use of collections of anti-tumor monoclonal antibodies which would have the benefit of using the same preexisting reagent on many patients. Although this would be a advantage, because individual tumors are so variable, the finding of multiple antigens specific to one cancer type present on all cancers of that type is not expected to be a common occurrence (D. Berd et al., Cancer Res. 49:6840–44, 1989). Even if an effective treatment using collections of monoclonal antibodies is found for patients with some types of cancer, it is unlikely to be an effective treatment for many forms of neoplasia.

Monoclonal antibody technology, in its present stage, has focused on the use of non-human monoclonal antibodies. This often presents a problem because patients develop antibodies to the non-human regions of the proteins including both the constant and variable regions. Antibodies reactive against the antigen binding site, the variable regions, of another antibody are called anti-idiotypic antibodies. Murine monoclonal antibodies, the easiest to produce and most prevalent, have been shown to induce a humoral response in humans which is referred to as the human anti-mouse antibody response or the HAMA response (D. L. Sawler et al., J. Immunol. 135:1530–35, 1985). Significant HAMA responses in patients receiving such therapy, besides destroying any possible benefit of the treatment, introduces numerous complications including immune complex disorders.

In recent years, these problems have been partially solved by the generation and use of chimeric antibodies. Chimeric antibodies have V regions derived from the tumor-specific mouse monoclonal antibody, but human C regions (S. L. Morrison and V. T. Oi, Adv. Immunol. 44:65–92, 1989). In such forms, the HAMA response is significantly reduced (although not eliminated), but there is still the anti-idiotypic response to deal with. Efforts to eliminate the anti-idiotypic response have involved the engineering of antibodies in which only the CDRs are derived from the mouse antibody and the framework and C regions are of human origin. These are the so-called humanized antibodies (P. C. Caron et al., Cancer Res. 52:6761–67, 1992). These antibodies are very difficult to create involving multiple cloning events and may still elicit anti-idiotypic antibodies (The Third Annual IBC International Conference on Antibody Engineering, Dec. 14–16, 1992, San Diego). Completely human monoclonal antibodies are presently being developed, with the hope that they will not elicit anti-idiotypic antibodies (C. J. Fisher et al., Critical Care Med. 18:1311–15, 1990). However, as mice are perfectly capable of generating anti-idiotypic antibodies to antibodies derived from the same species and even from the same inbred strain, the generation of anti-idiotypic antibodies after the injection of large amounts of antibodies with identical V regions will remain a problem as long as monoclonal antibodies are used.

The use of polyclonal antibodies would overcome some of the drawbacks associated with monoclonal antibody therapy. Unlike monoclonal antibodies, polyclonal antibodies are directed to many different antigenic determinants on the target cell surface and would bind with sufficient density to allow the effector mechanisms of the immune system to work efficiently possibly eliminating any need for radioactive or toxic tags. Furthermore, the chance that tumor cell escape variants which have lost reactivity with all of the polyclonal antibodies would arise is exceedingly small. Anti-idiotypic reactivity in patients is not expected to be a problem because no one V region combination should be present in sufficient quantity to elicit a significant response.

There are several problems associated with the use of conventional polyclonal antibodies. First, polyclonal antibodies in the form of gamma globulin, is available in a very limited supply, insufficient for widespread human treatments. Second, when used on a patient, many of the polyclonal antibodies will be absorbed by the patient's normal cells and tissues. The number of different antibodies which remain after absorption would be exceedingly small, possibly too small to be of any beneficial effect. Thirdly, this supply, besides being inadequate, requires a great deal of purification to remove unwanted materials, such as cytokines and other immunoregulatory proteins, which may elicit undesirable immune responses and side effects. There is also a substantial risk of contamination associated with infectious organisms such as HIV or toxins such as lipopolysaccharide, which may be present in the source. These problems are difficult to overcome because of composition variability as the material is collected from many different biological sources. Recombinant production of polyclonal antibodies would address certain of these issues, but the genes encoding these antibodies are not readily identifiable and the technology to efficiently work with collections of antibody genes has yet to be developed.

Recently, antigen-binding antibody fragments have been expressed on the surface of filamentous phage (G. P. Smith, Sci. 228:1315, 1985). Libraries of H and L variable region cDNAs have been obtained from animal and human B cells and cloned in pairs in random H–L combinations into phage display vectors to produce combinatorial libraries displaying Fab or single-chain Fv fragments (W. D. Huse et al., Sci. 246:1275–81, 1989). Fab is formed by the association of L chain with the $V_H$ and $C_{H1}$ domains of the H chain, the Fd region. In phage display libraries, the carboxyl-terminal end of the Fd or Fv region is tethered to a fragment of a phage coat protein, such as cpIII or cpVIII, which anchors the Fab fragment to the surface of the phage. In both Fab and Fv fragments, as in the intact antibodies, the antigen-binding site is formed from the combination of the $V_H$ and $V_L$ domains.

Phage display libraries can be selected for binding to specific antigens by affinity chromatography (R. E. Hawkins et al., J. Mol. Biol. 226:889, 1992) or by panning phage on antigen-coated surfaces (C. F. Barbas et al., Proc. Natl. Acad. Sci. USA 88:4363, 1991). As the DNA segments encoding the selected antibody fragments are carried by phage particles, the selected phage particles encoding monoclonal antibody fragments can be isolated and propagated indefinitely. The selected phage clones can be modified to produce antibody fragments devoid of the coat protein moiety that may also be secreted from the bacterial cells. Antibody fragments specific for haptens, proteins and several human viruses have been recovered from such phage display combinatorial libraries (J. D. Marks et al., J. Mol. Biol. 222:581, 1991; R. A. Williamson et al., Proc. Natl. Acad. Sci. USA 90:4141, 1993).

One major drawback of these combinatorial libraries is that the $V_H$ and $V_L$ regions which form the antigen binding domain are randomly associated. The original combinations of H and L chains that were so efficiently selected in vivo by the antigen are lost (J. McCafferty et al., Nature 348:552–54, 1990). The chance of finding H and L combinations with high affinity for the antigen of interest is very small. The number of clones that would need to be screened for the presence of specific binding to the antigen is increased by orders of magnitude.

A method for amplifying and linking the expressed $V_H$ and $V_L$ region genes within single cells in a population of cells has been very recently reported (M. J. Embleton et al., Nuc. Acids Res. 20:3831–37, 1992). This method was exemplified with two mouse hybridoma cell lines, each producing a known and distinct immunoglobulin (Ig) product. The two cell populations were mixed, fixed with formaldehyde and permeabilized with the detergent NP-40. cDNAs were synthesized using reverse transcriptase and primers complementary to the 3' ends of the $V_H$ and $V_L$ mRNAs. The cDNAs were then amplified by PCR and linked in the same reaction using, in addition to the cDNA primers, one primer from the 3' end of the $V_H$ gene and one primer from the 5' end of the $V_L$ gene. These primers also contained complementary tails of extra sequence for the self-assembly of the $V_H$ and $V_L$ genes. In a second PCR, after washing the cells, the linked $V_H$ and $V_L$ region genes were amplified with terminal nested primers yielding a population of DNA fragments which encoded the $V_H$ and $V_L$ sequences in a head-to-tail transcriptional orientation. These DNA fragments were recovered from the cell supernatants.

Although this report claimed that almost all $V_H$–$V_L$ combinations examined were derived from only one of the hybridoma cell lines, the method results in mixed $V_H$–$V_L$ combinations wherein $V_H$ and $V_L$ can be derived from different cells. That $V_H$–$V_L$ mixing should occur is also apparent from theoretical considerations. As the linked $V_H$–$V_L$ combinations are recovered from the supernatant of the fixed/permeabilized cells, the pores in the membranes of these cells allow free passage of such linked DNA molecules, one would expect that the smaller $V_H$ and $V_L$ DNA molecules could exit the cells and become linked and be further amplified outside the cells where free mixing of $V_H$ and $V_L$ from different cells would occur.

SUMMARY OF THE INVENTION

The present invention overcomes the problems and disadvantages associated with current strategies and designs and provides new compositions and methods for the prophylaxis and treatment of certain diseases and disorders.

Polyclonal antibody libraries have a higher complexity than monoclonal antibodies or antibody cocktails, being directed against many different antigenic determinants and carry the option to use radioactive, toxin, and other tags for both therapy and diagnosis. One embodiment of the invention is directed to methods for treating neoplastic disorders using polyclonal antibody libraries specifically directed to a disease or disorder. A sample of neoplastic tissue is obtained from a patient. The sample is introduced to a cell population capable of producing antibodies such as the spleen cells of a mammal. The cell population is fixed, permeabilized and the $V_H$ and $V_L$ mRNA molecules reverse transcribed into $V_H$ and $V_L$ cDNA sequences. The cDNA sequences are PCR amplified and the amplified sequences linked, preferably in a head-to-head transcriptional orientation. The linked sequences are again PCR amplified to create a population of DNA fragments which encode the $V_H$ and $V_L$ antibody regions. These DNA fragments are cloned into expression vectors and the different populations of expression vectors expanded in the transfected host. Expression vectors which encode a library of recombinant anti-neoplastic antibodies are selected and the subpopulations or sublibraries expanded again. The recombinant anti-neoplastic antibodies produced by these vectors are then administered to the patient. The neoplastic disorders which can be treated include leukemias, lymphomas, sarcomas, carcinomas, neural cell tumors, squamous cell carcinomas, germ cell tumors, metastases, undifferentiated tumors, seminomas, melanomas, neuroblastomas, mixed cell tumors, neoplasias caused by infectious agents and other malignancies.

Another embodiment of the invention is directed to the in vivo diagnosis of a neoplastic disorder by imaging the diseased tissue in a patient. A library of patient-specific, anti-neoplastic antibodies are created, as described herein, and labeled with a detectable label. The antibodies may be whole or fragments of antibodies such as Fab fragments. The labeled library is administered to the patient and the label detected using, for example, radioactive detectors, visual inspection, nuclear magnetic resonance (NMR) detection, or other means to detect the appearance of label in a bodily tissue or waste, or within the whole body itself. From these methods, heretofore unidentified neoplasias may be perceived which escaped detection by other means. Also, once detected the neoplasia can be effectively monitored during treatment regiments.

Another embodiment of the invention is directed to methods for creating patient-specific or antigen-specific libraries of polyclonal antibodies. These libraries, created as described above, are useful for the treatment or prophylaxis of a number of diseases including neoplasia, malignancies, infections, genetics defects and genetic deficiencies. Libraries may comprise vectors containing DNA encoding the variable regions, DNA encoding the entire antibody, or antibodies or antibody fragments. Once isolated and cloned, the library can be expanded to ensure the representation of every member of the antigenic profile and can also be easily transferred to other vectors.

Another embodiment of the invention is directed to compositions containing libraries of polyclonal antibodies or genetic expression vectors which encode these antibodies. The library or selected sub-library of antibodies may be labeled with a detectable label and/or contain a pharmaceutically acceptable carrier. Compositions can be administered to patients for diagnostic or treatment protocols. Alternatively, libraries of vectors may be administered to patients for the in vivo expression of antibodies or antibody fragments.

Another embodiment of the invention is directed to diagnostic aids or kits and methods for using these kits for the detection of diseases and disorders. Diagnostic aids or kits comprise a polyclonal antibody library which may be labeled with a detectable label to which is added a sample suspected of containing the target antigen. The sample may be a sample of bodily fluid such as blood, serum, plasma, spinal fluid, lymph or urine. The presence of absence of the target antigen indicates the presence of a particular disease, disorder or contaminant. Samples may be biological samples from a patient or biological samples from an environmental source suspected of harboring a contaminant. Sample is mixed with the library and the presence of antigen confirmed by the binding of a significant number of antibodies and detection of the label.

Another embodiment of the invention is directed to methods for creating and utilizing libraries of receptor proteins which possess variable regions. Receptor proteins which may be utilized to create a library include T-cell receptors, B-cell receptors, natural killer cell receptors and macrophage receptors. A sample of biological tissue is introduced to a cell population capable of producing receptor proteins. Variable region receptor protein mRNAs are reverse transcribed into cDNA sequences which are PCR amplified and the resulting DNA fragments cloned into expression vectors. The expression vectors which encode the recombinant receptor proteins are selected and a subpopulation selected expanded to produce the library. These libraries can be used to diagnose, image or treat diseases and disorders including neoplasias, infections and genetic defects and deficiencies. In addition, using these same methods libraries of chimeric proteins containing both antibody and receptor protein portions may also be created and utilized.

Another embodiment of the invention is directed to nucleic acid vectors which can be used to create the antigen-specific polyclonal antibody libraries. These vectors comprise restriction enzyme recognition sites convenient for the cloning of nucleic acid fragments and sequences to efficiently PCR amplify the cDNA fragments. The vectors are designed to have one or more pairs of genetic fragments inserted in a head-to-head transcriptional orientation and, optionally, further comprise transcription and translation controlling sequences such as TATA boxes, CAT boxes, ribosome binding sites, RNA polymerase initiation and termination sites, leader sequences, strong transcriptional promoters which may be differentially regulated or parts or combinations thereof.

Another embodiment of the invention is directed to methods for transferring a library of nucleic acid fragments between different vectors without significant loss of library diversity. The library of fragments is inserted into first vectors in a head-to-head transcriptional orientation to form recombinant vectors. The inserts of these recombinant vectors are transferred into second vectors by, for example, PCR amplification of the inserted sequences or restriction enzyme cloning, and the fragments reinserted into second vectors without significant loss of library diversity.

Other embodiments and advantages of the invention are set forth, in part, in the description which follows and, in part, will be obvious from this description or may be learned from the practice of the invention.

DESCRIPTION OF THE DRAWINGS

FIG. 3. Partial maps of phagemid expression vectors (a) pComb3, (b) phh3, (c) plPPl, and (d) phh3mu or phh3hu, shown not to scale. Amino acids AQVKL (SEQ ID NO: 11) and LKVQL (SEQ ID NO: 10) contributed by the vectors are shown in one letter code in front of the Fd and L chain genes. P=promoter; l=leader sequence; lmod=leader sequence with modified nucleotide sequence.

FIG. 8. Cell supernatant analysis by (a) Western blot and (b) ELISA.

FIG. 10. Generation of (a) bacterial and (b) mammalian vectors for expression of Fab phage-display libraries or intact antibodies derived from head-to-head linked $V_H-V_L$ combinations. The amino acids AQVKL (SEQ ID NO: 11) are contributed by the vector.

DESCRIPTION OF THE INVENTION

Figure 1:
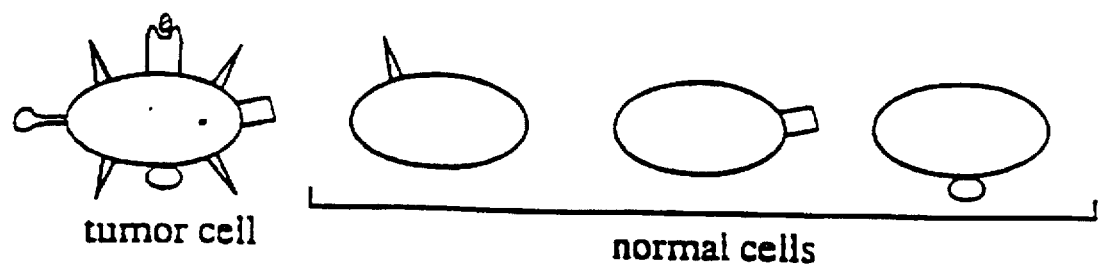
FIG. 1. Schematic comparison of the differences in density and diversity of antigens on the surface of normal versus tumor cells.

As embodied and broadly described herein, the present invention comprises methods for the creation and use of libraries of related proteins such as antibodies, receptors including T cell receptors, and other immune related proteins.

During an immune response many thousands of different B cell clones, specific for each antigenic determinant, are generated and proliferate creating a large diversity of antibodies. This diversity is further increased by somatic hypermutation mechanisms that function on the antigen-stimulated B cells. These very efficient processes, which operate during maturation of the immune response, result in a very large selection of antibodies with increased affinity for antigen. However, current antibody therapy has focused on the use of monoclonal antibodies and when B cell clones are immortalized by hybridoma formation, only a small fraction of the B cell clones are represented. Further, because only dividing cells can participate in formation of stable cell hybrids, terminally differentiated plasma cells which produce high affinity antibodies are probably not represented in the population.

One embodiment of the invention is directed to methods for treating neoplastic disorders using patient-specific or disease-specific anti-tumor libraries of polyclonal antibodies. Such libraries are expected to encompass the full-spectrum of an antibody response to tumor cells much more efficiently than hybridoma produced monoclonal antibodies or monoclonal antibody cocktails. These libraries are also readily reproducible and can be created and maintained with all of the diversity associated with a natural immune response intact. Although the complexity of each polyclonal antibody library is not immediately known, it is expected to be very high and carry with it the ability to activate all of the effector functions associated with an immune response.

A library is created by obtaining a sample of neoplastic tissue from a patient with a particular disorder. The neoplastic tissue may be derived from tumor tissues, blood and blood related tissues, biopsied tissues, cancerous tissues, malignant tissues, metastasized tissues and combinations thereof. Samples may be obtained from biopsy of diseased tissue, primary or immortalized cell culture of related cell types, or cells which are artificially stimulated to present a particular antigenic profile. Neoplastic tissue may also be first propagated in an immunodeficient animal such as a mouse model to bolster the unhindered expression of antigen. Useful mouse models include the nude mouse, the SCID mouse and the irradiated mouse. Congenital athymic nude mice, deficient in T cell function, allow for the in vivo growth of human tumors. Severe combined immunodeficient (SCID) mice which lack functional B and T cells, and sub-lethally irradiated mice where the T and B cells have been destroyed have also been shown to allow the growth of allogeneic and xenogeneic tumors. Nude mice and SCID mice are permissive for the growth of normal human cells and can be reconstituted with human peripheral blood leukocytes (Hu-PBL) by, for example, intraperitoneal (i.p.) injection of about $1-5 \times 10^7$ cells.

Alternatively, the neoplastic tissue may be subjected to purification to obtain a single target antigen, group of antigens or antigen-containing extract. This approach is especially useful when there exists a risk of carrying unwanted or dangerous components from living or killed cells into the procedure, or simply for convenience or storage considerations. For example, when human blood cells are utilized there is a risk of carrying infectious virus, such as HIV-I or hepatitis virus, and it would be desirable to eliminate that risk. Extracts are prepared from the cells which have a highly reduced concentration of normal antigens and/or an increased concentration of neoplastic antigens. Cell surface, membrane or whole cell extracts would generally be preferred and can be prepared and stored at 4° C., -20° C., -80° C., or in liquid nitrogen, or lyophilized and stored at about room temperature. Methods for protein purification and the preparation of extracts are well-known to those of ordinary skill. Many of these procedures are described in *Guide to Protein Purification* (Methods in Enzymology, vol. 182, M. P. Deutscher editor, Academic Press, San Diego, Calif., 1990), whose disclosures are hereby specifically incorporated by reference. Lastly, sample antigen may also be made synthetically using organic chemistry techniques when appropriate or convenient.

The sample of neoplastic tissue or antigen is then introduced, either in vitro or in vivo, to a cell population capable of producing antibodies. Useful in vitro cell populations include murine cells, ovine cells, porcine cells, primate cells, human cells, transformed, fused or immortalized cells, and combinations thereof. Antibody producing cells are removed from an animal, or cell culture, and exposed to antigen. The antigen-stimulated cells can be used directly or can be fused with an immortalized cell line such as a myeloma to generate a population of antibody producing hybridomas. In vivo culturing techniques are preferred and involve the direct injection of sample into an animal containing a responsive population of antibody producing cells. The animal may be a human or other primate, mouse, goat, rabbit or other mammal. When using animals, multiple injections with adjuvant are the preferred procedure as this often leads to a high concentration of antigen-specific antibody producing cells with very strong affinity for the antigen. The antibody producing cells, usually obtained from the spleen, but possibly from peripheral blood or lymph, can then be easily isolated surgically, nonsurgically or otherwise as appropriate.

Antigen stimulated antibody producing cells, obtained from either in vivo or in vitro sources, such as after fusion with a myeloma or hybridoma cell line, are fixed with a fixative solution such as Streck Tissue Fixative (Streck Labs; Omaha, Nebr.), or a solution containing a chemical such as carbohydrazide, glutaraldehyde, or osmium tetroxide, but preferably formaldehyde or combinations of these chemicals. For example, between $10^4$ to $10^8$ pelleted cells are suspended in 0.1 to 2.0 mls of 10% formaldehyde solution plus 0.15M NaCl. Cells are kept on ice for a period of time, washed and pelleted. These fixed cells are next permeabilized with a permeabilizing solution comprising chemicals such as Nonidet P-40 (NP-40), Brij, Tween, for example tween-20, polysorbate, Triton X-100 (TX-100), CHAPS, sorbitan or combinations thereof. For example, the permeabilization solution may comprise about 0.5% NP-40 which is added to the fixed cell pellet, and the mixture incubated on ice for a period of time, washed, pelleted and the pellet dispersed into PBS containing 0.1M glycine to maintain the overall cell structure. Alternatively, permeabilization may comprise treatment of the fixed cells with enzymes such as proteinase K. The fixing and permeabilizing should provide suitable porosity to the cells to allow the entrance of enzyme without undue destruction of the cellular compartment or of the nucleic acids within the compartment. Permeabilization permits enzymes, nucleotides and other necessary reagents to enter the individual cells, now fixed cellular compartments, to reverse transcribe cellular $V_H$ and $V_L$ mRNA into $V_H$ and $V_L$ cDNA sequences. The solid support may be any support which is suitable and not detrimental to the procedure such as a glass or plastic surface, or membrane polymer. Cells should be in as concentrated a space as possible to minimize overall volume. Decreased volume allows for smaller amounts and more concentrated solutions of enzymes to be added.

Reverse transcription may be performed in a single step or in an optional combined reverse transcription/PCR procedure. The first enzyme solution comprises, for example, reverse transcriptase such as AMV or MMTV reverse transcriptase, a balanced salt solution including Tris-HCL, pH 8–8.5, dithiothreitol (DTT), potassium chloride (KCl), and magnesium chloride ($MgCl_2$), sufficient quantities of all four dNTPs, and primers which bind to the mRNA providing a 3'-hydroxyl group for reverse transcriptase to initiate polymerization. Optionally, an RNase inhibitor such as RNasin (Promega; Madison, Wis.) may be added to prevent RNA breakdown. Although any primer sequence which is complementary to the mRNA may be used, to facilitate selection of variable region messages, primers complementary to the 3'-terminus of $V_H$ and $V_L$ mRNA molecules would be preferred. First strand synthesis is performed, for example, at about 42° C. for about 60 minutes. Molecular biological procedures for optimizing enzymatic procedures such as these and others described herein in the practice of the invention are disclosed in *Current Protocols in Molecular Biology* (F. M. Ausubel et al. editors, John Wiley & Sons, NY, 1989). After completion of the reaction, cells are pelleted, washed to remove reaction reagents, and resuspended in PBS.

The resulting cDNA sequences are PCR amplified using primers specific for immunoglobulin genes and, preferably, for the terminal regions of the $V_H$ and $V_L$ nucleic acids. Methods of PCR amplification are disclosed in U.S. Pat. No. 4,683,195, which is hereby specifically incorporated by reference. Preferably, the cDNAs are PCR amplified and linked in the same reaction, using, in addition to the cDNA primers, one primer for the 5' end of the $V_H$ region gene and another for the 5' end of the $V_L$ gene. These primers also contain complementary tails of extra sequence, to allow the self-assembly of the $V_H$ and $V_L$ genes. After PCR amplification and linking, the chance of getting mixed products, in other words, mixed variable regions, is minimal because the amplification and linking reactions were performed within each cell. The risk of mixing can be further decreased by utilizing bulky reagents such as digoxigenin labeled nucleotides to further ensure that V region cDNA pairs do not leave the cellular compartment and intermix, but remain within the cell for PCR amplification and linking. The amplified sequences are linked by hybridization of complementary terminal sequences. After linking, sequences may be recovered from cells. For example, after linking, cells can be washed in a solution of sodium dodecyl sulfate (SDS). The SDS precipitates out of the cells after incubation on ice and the supernatant can be electrophoresed into an agarose or acrylamide gel. Alternatively, or in combination with the SDS process, using a reagent such as digoxigenin-linked nucleotides, DNA products synthesized will remain within the cell and be amplified. The linked product is recovered upon electrophoresis of the supernatant.

After electrophoresis of the supernatant, the gel slice corresponding to the appropriate molecular weight of the linked product is removed and the DNA isolated on, for example, silica beads. The recovered DNA can be PCR amplified using terminal primers, if necessary, and cloned into vectors which may be plasmids, phages, cosmids, phagemids, viral vectors or combinations thereof. Convenient restriction enzyme sites may be incorporated into the hybridized sequences to facilitate cloning. These vectors may also be saved as a library of linked variable regions for later use.

Alternatively, after recovery of sequences from washed cells, the linked $V_H$ and $V_L$ region genes are PCR amplified a second time using terminal nested primers, yielding a population of DNA fragments which encode the linked $V_H$ and $V_L$ genetic regions. These DNA fragments are recovered from cell supernatants. The grouping of $V_H$ and $V_L$ combinations is an advantage of this process and allows for the in mass or batch transfer of all clones and all DNA fragments during this and all cloning procedures. Preferably, the $V_H$ and $V_L$ cDNAs are linked in a head-to-head transcriptional orientation (←→), as opposed to a head-to-tail orientation (→→ or ←←). This transcriptional orientation allows for the easy transfer of V region pairs between vectors and for the production of intact antibodies or antibody fragments such as Fab fragments, without loosing the original H and L chain combinations that were present in the original population of polyclonal antibodies.

Further, this cloning orientation allows for the grouping of transcriptional controlling sequences in a single region and controlled expression of each gene. The single control region can be created as a cassette, engineered with multiple restriction enzyme sites to be easily transferred between different vectors. Also, having the linked sequences in a head-to-head transcriptional orientation allows for a single-step bulk transfer of DNA fragments encompassing both variable regions into an expression vector. Head-to-tail orientations generally require multiple cloning steps.

It may sometimes be desirable to treat the variable region gene sequences with a mutating agent. Mutating agents create point mutations, gaps, deletions or additions in the genetic sequence which may be general or specific, or random or site directed. Useful mutating agents include ultraviolet light, gamma irradiation, chemicals such as ethidium bromide, psoralen and nucleic acid analogs, or DNA modifying enzymes such as restriction enzymes, transferases, linases and specific and nonspecific nucleases and polymerases. In particular, random mutations may be introduced in the CDRs of the $V_H$ and $V_L$ region genes by oligonucleotide directed mutagenesis. Mutations introduced into the gene sequence will ultimately increase library complexity and diversity as well as affinity for antigen which may further increase the library's usefulness in treatment. Furthermore, such mutagenesis may be used on a single $V_H$-$V_L$ pair or on a defined group of such pairs to generate a library de novo.

Cloning is performed, for example, by cleaving the cDNA and vector sequences with a restriction enzyme, if necessary isolating certain nucleic acid fragments, mixing the fragments together in the presence of ligase in a suitable balanced salt solution, and incubating the mixture under enzymatically acceptable conditions for a prescribed period of time. Using different enzyme recognition sites at each terminus of the cDNAs, cloning orientation can be predetermined. Vectors are transformed into acceptable host cell cultures and the cultures amplified to expand the different populations of vectors which comprise the library. Host cells for prokaryotic vectors may be a culture of bacteria such as *Escherichia coli*. Host cells for eukaryotic vectors may be a culture of eukaryotic cells such as any mammalian, insect or yeast cell lines adapted to tissue culture. Bacterial cells are transformed with vectors by calcium chloride-heat shock or electroporation. Eukaryotic cells are transfected with calcium phosphate precipitation or electroporation, although many different transformation procedures which would also be acceptable. The DNA fragments may be cloned into prokaryotic or eukaryotic expression vectors, chimeric vectors or dual vectors. The expression vector may be a plasmid, cosmid, phage, viral vector, phagemid and combinations thereof, but is preferably a phage display vector wherein the recombinant product is expressed on the phage surface to facilitate screening and selection. Useful transcriptional and translational sites may be placed on the expression vector including RNA polymerase recognition regions such as a TATA box site, a CAT site, an enhancer, appropriate splicing sites, if necessary, a AT rich terminal region and a transcription initiation site. Useful sites to facilitate translation include translational start and stop sites and ribosome binding sites. Typically, some of the more useful sites for efficient eukaryotic expression, such as the SV40, CMV, HSV or baculovirus promoter/enhancer region, are derived from viruses. The resulting recombinant antibody may be of the murine class $IgG_1$, $IgG_{2A}$, $IgG_{2B}$, IgM, IgA, IgD or IgE, the human classes $IgG_1$, $IgG_2$, $IgG_3$, $IgG_4$, IgM, $IgA_1$, $IgA_2$, IgD or IgE, or combinations or fragments thereof. Preferably, the chimeric antibody library is composed of primarily IgG antibodies or Fab antibody fragments.

Amplification of the population of vectors is performed by incubating and expanding the recombinant cell cultures. Bacterial cell cultures are grown in, for example, L-broth at 37° C., overnight. Eukaryotic cells are incubated at, for example, 37° C. in a high humidity, $CO_2$ incubator for 1–7 days or longer per passage. At this point, library complexity is expected to be fairly high with large numbers of vectors for every different vector population. The population contains a representative nucleic acid sequence for every or nearly every variable region which was created in response to the initial antigen.

A feature of the invention is the ease by which pairs of genetic elements, containing intact and expressible variable regions, can be transferred within and between vectors such as prokaryotic, eukaryotic and mammalian vectors. Entire libraries or sub-libraries can be transferred with equal efficiency. Transfer is accomplished by opening, preferably with restriction enzymes for site specificity, the vector between the coding regions for the amino termini of the variable region proteins. Cassettes containing promoter and leaders sequences in a head-to-head orientation (leader-promoter-promoter-leader; lPPl), which may be prokaryotic or mammalian, can be inserted in this area to replace the existing controlling region or as a first controlling region. The DNA stretches comprising the variable region genes and the lPPl cassette is then PCR amplified using appropriate primers and transferred between vectors. Batches of linked V-regions with or without the promoter-leader regions, such as entire libraries or parts of libraries, can be quickly and easily transferred as desired. These DNA segments can be incorporated into the DNA of phage display vectors for rapid analysis, of cosmids for long term storage, or of mammalian expression vectors for subsequent expression. Expression may be for production of the polyclonal antibodies or screening of surface display libraries, which may be prokaryotic or eukaryotic, to isolate one or more sub-libraries. Another feature of the invention is the ability to incorporate extra sequences into the vectors to facilitate handling such as with additional restriction enzyme sites, or additional transcriptional or translational regulatory regions to facilitate or further control protein expression.

Libraries of expression vectors, mammalian or bacterial, which encode recombinant anti-neoplastic antibodies, or antibody fragments, can be selected into sub-libraries by adsorbing the recombinant particle, which may be a eukaryotic or prokaryotic cell or virus, against a neoplastic or non-neoplastic tissue. Selection will reduce overall library complexity, but antigen-specific complexity of the sub-library should not be significantly effected. The tissue may be another sample of the same tissue from which the antibody producing cells were exposed or another tissue from a different or the same patient. For example, non-neoplastic tissue from the same patient may be most useful to remove non-neoplastic antigen binding antibodies expressed on the surface of displaying phage. Alternatively, neoplastic tissue from the same or a different patient with the same disorder may be most useful to isolate the specific anti-neoplastic antibodies. In either situation, tissue or antigen may be fixed to a solid support and the expression vectors in-mass subjected to, for example, affinity chromatography techniques, isolating either the flow through or washes as desired. Also, the vector population may be screened by, for example, Western blotting of expressed antigen, or Southern or Northern blotting to identify nucleic acid. The resulting selected vectors, or sub-libraries, are amplified by culturing and expanding the population of the host organism. If necessary, DNA fragments in bacterial expression vectors may be transferred to mammalian expression vectors as, for example, cassettes because the linked regions created are flanked with restriction enzyme sites. A feature of this aspect of the invention is that greater than 99.9% of the library may be removed during selection, but the remaining population of vectors, the subpopulation, can still be amplified to create large numbers of vectors or amounts of protein. Effectively, none of the specific complexity of the selected or sub-library is lost, and further, this sub-library can be transferred intact and in bulk between vectors just as easily as the original library.

The expanded and amplified populations of expression vectors selected can be stored for later use, administered to a patient directly, if safety conditions permit, or the products transcribed and translated and the anti-neoplastic antibodies expressed administered to the patient. Administration may be by parenteral, sublingual, rectal or enteral routes. Parenteral administration is usually preferred which includes intravenous (i.v.) injection, subcutaneous (s.c.) injection, intramuscular (i.m.) injection, intra-arterial injection, intrathecal injection, intraperitoneal (i.p.) injection, or direct injection into a site of the neoplasm. Either antibodies or vectors may be administered, but the administration of antibodies is preferred because efficient expression from the vector may be an additional complication, or there may be safety concerns associated with introducing recombinant vector DNA into the animal.

Neoplastic disorders which are treatable by these methods are many and include leukemias, lymphomas, sarcomas, carcinomas, neural cell tumors, squamous cell carcinomas, germ cell tumors, metastases, undifferentiated tumors, seminomas, melanomas, neuroblastomas, mixed cell tumors, neoplasias caused by infectious agents and other malignancies. The ubiquitous nature of the method is due, in part, to its ability to utilize samples of almost any antigen. Preferably the patient treated is a human, but any mammal with a functional humoral immune system is also treatable. Patients may be treated therapeutically or prophylactically, as necessary, according to prescribed protocols. For example, certain cancers go through successive cycles of progression and regression over months or years. Libraries can be prepared and administered shortly before the progressive stage to inhibit growth of the cancer, invasion of other tissues, or the process of metastasis. Libraries may also be administered as a bolus to eliminate the cancer at a single dose or with a number of doses.

The library may also be administered in conjunction with an anti-neoplastic agent which augments the patient's own immune system such as a T cell growth factor, B cell growth factor, granulocyte/macrophage growth factor, granulocyte growth factor, macrophage growth factor, stem cell growth factor, transforming growth factor, erythropoietin, steel factor, bone morphogenic protein, differentiating agent, interleukin, interferon, hormone, component of the complement system, or a combination thereof. The patient's treatment protocol may also involve other forms of therapy such as chemotherapy, radiation therapy, diet or immunotoxin therapy. Useful chemotherapeutic agents include alkylating agents, purines and pyrimidine analogs, vinca and vinca-like alkaloids, etoposides and etoposide-like drugs, antibiotics, corticosteroids, nitrosoureas, antimetabolites, platinum based cytotoxic drugs, hormonal antagonists, anti-androgens, and anti-estrogens. These treatments may be incorporated into an overall protocol for treatment of the patient's neoplasia.

Immunotoxic therapy may be facilitated by the methods disclosed herein. For example, recombinant DNA fragments which encode both the $V_H$ and $V_L$ antibody fragments may be cloned into expression vectors which encode the antibody constant region and a toxic substance. The expressed fusion products will, therefore, have a high number of different antibodies to the target neoplasia, each of which is linked to a toxic substance such as an animal, plant, bacterial, fungal, viral or parasitic toxin. Administration of the antibody library to the patient will, in addition to recruiting the host's immune defenses, bring the toxin into direct contact with the diseased cell which may facilitate destruction of the neoplasia. Especially useful toxic substances include toxins derived from certain plants and bacteria such as the Pseudomonas toxins, Diphtheria toxins, Escherichia toxins and ricin.

Another embodiment of the invention is directed to a method for imaging a neoplastic disorder in a patient. A library of patient-specific, anti-neoplastic antibodies are created as described above and mixed with a pharmaceutically acceptable carrier such as water, a salt or buffered solution, glycerol, oil, a saccharide or polysaccharide, cellulose or starch, alcohol or combinations thereof. The antibodies of the library are labeled with a detectable label and administered to the patient. The antibodies migrate throughout the body and bind to the target which may be the neoplasia or neoplastic metastasis and the label imaged in the patient. Detectable labels which may be useful for this procedure include radioisotopes, stable isotopes, enzymes, fluorescent compounds, luminescent compounds, chromatic compounds, metals or electrical charges. The now labeled neoplasia may be detected by means suitable for the label such as with a geiger counter, nuclear magnetic resonance (NMR) imager, visual detectors or simply on sight, or by autoradiography.

Another embodiment of the invention is directed to a composition comprising a patient-specific library of anti-neoplastic antibodies or antibody fragments and a pharmaceutically acceptable carrier. Composition are administered to patients with the characteristic neoplasia to which the antibodies created were directed. The pharmaceutically acceptable carrier is a compound or medium which facilitates administration, increases storage life of the composition, or increases the composition's usefulness to the patient, such as by increasing circulating or serum half-life. Useful carriers include water, saline, alcohol, glycols including polyethylene glycol, oil, polysaccharides, salts, glycerol, stabilizers, emulsifiers and combinations thereof. The composition may comprise antibodies or antibody fragments, preferably Fab fragments, selected from the group consisting of the murine classes $IgG_1$, $IgG_{2A}$, $IgG_{2B}$, IgM, IgA, IgD and IgE, the human classes $IgG_1$, $IgG_2$, $IgG_3$, $IgG_4$, IgM, $IgA_1$, $IgA_2$, IgD and IgE, and combinations or fragments thereof. The composition may also be preserved over long periods of time by dialysis or lyophilization of the proteins to remove all liquid. Lyophilized antibodies may be stable at room temperature for years.

Another embodiment of the invention is directed to methods for creating and utilizing a library of antigen- or tissue-specific polyclonal antibodies or antibody fragments as described above. A sample of biological tissue or antigen, naturally, recombinantly or synthetically isolated, is obtained, possibly from the patient to be treated or a patient with a related disorder. The biological tissue or antigen used to stimulate the antibody producing cells may be derived from tumor tissues, blood and blood related tissues, biopsied tissues, infected tissues, bacteria, virus, fungi, parasites, malignant tissues, genetically abnormal tissues or combinations thereof, or from an environmental source such as a body of water, soil, man-made or natural waste or biomass. The sample is introduced to a cell population capable of producing antibodies. The $V_H$ and $V_L$ mRNA of the cell population are reverse transcribed into $V_H$ and $V_L$ cDNA sequences which are PCR amplified with the resulting amplified sequences linked. The linked sequences are PCR amplified to create a population of DNA fragments which encode $V_H$ and $V_L$ antibody fragments that are cloned into expression vectors, and the population of cloned expression vectors expanded. The expression vectors which encode antigen- or tissue-specific antibodies or antibody fragments may be selected and the subpopulation selected expanded to produce the library. The library of polyclonal fragments may be cloned in-frame into other expression vectors which encode antibody constant region gene sequences to express polyclonal antibodies or antibody fragments. These antibodies can then be intravenously or subcutaneously injected for systemic infections, applied directly to a wound for localized treatment, or otherwise administered to the patient as needed.

Disease-specific or antigen-specific libraries can be used in methods to treat or prevent such disorders as viral, fungal, parasitic or bacterial infections, genetic abnormalities and intoxications. For example, libraries of antibodies to the gp120 protein of the HIV-1 virus, which causes the autoimmune deficiency syndrome (AIDS), may be created and administered to AIDS patients to reduce virus-induced cell death, viral load or infectivity, or as a prophylaxis to prevent a possible infection after an exposure or when there is a risk of exposure. Libraries can be used to replace or supplement other forms of passive immune therapy such as gamma globulin treatments for such diseases as rabies, hepatitis, varicella-zoster virus, herpes or rubella. For example, an anti-rubella library may be administered periodically as needed to pregnant women who are at risk of contracting rubella from another family member. It is safe of harmful side effects and effective. Anti-herpes antibodies could be administered to uninfected individuals of infected partners. Meningitis can be a life-threatening disease, especially in children, because effective treatment cannot always be determined and administered quickly. In contrast, libraries of anti-meningitis polyclonal antibodies can be stored and used when cases are suspected because the risk of treatment complications is very low. Polyclonal antibodies created by these methods may supplement conventional influenza vaccines by providing protection against influenza for a short term until the host's own immune system can build a sufficient antibody response to the antigen.

Polyclonal libraries can also be useful as prophylaxis or treatment in burn patients who are susceptible to a wide variety of hospital-acquired infections from, for example, Staphylococcus, Streptococcus, Hemophilus, Neisseria, Pseudomonas and the actinomycetes. Libraries can be used to treat or prevent, or ameliorate the symptoms associated with, bacterial sepsis by creating and administering libraries directed against lipopolysaccharide (LPS), lipid A, tumor necrosis factor or LPS binding proteins. Other intoxications may also be treated with polyclonal antibody libraries such as gastrointestinal disorders induced by bacterial or viral microorganisms, toxicosis produced by yeast or other mycotic infections, or environmentally induced intoxication from harmful metals such as lead or aluminum, pesticides, industrial wastes, carcinogens, and other harmful organic or inorganic compounds.

Another embodiment of the invention is directed to a diagnostic kit for the detection of a disease or disorder in a patient, or a contaminant in the environment comprising a library of antigen-, tissue- or patient-specific antibodies or antibody fragments. The diagnostic kit can be used to detect diseases such as bacterial, viral, parasitic or mycotic infections, neoplasias, or genetic defects or deficiencies. The biological sample may be blood, urine, bile, cerebrospinal fluid, lymph fluid, amniotic fluid or peritoneal fluid, preferably obtained from a human. Libraries prepared from sample obtained from the environment may be used to detect contaminants in samples collected from rivers and streams, salt or fresh water bodies, soil or rock, or samples of biomass. The antibody may be a whole antibody such as an IgG or an antibody fragment such as an Fab fragment. The library may be labeled with a detectable label or the kit may further comprise a labeled secondary antibody that recognizes and binds to antigen-antibody complexes. Preferably, the detectable label is visually detectable such as an enzyme, fluorescent chemical, luminescent chemical or chromatic chemical, which would facilitate determination of test results for the user or practitioner. Diagnostic may further comprise agents to increase stability, shelf-life, inhibit or prevent product contamination and increase detection speed. Useful stabilizing agents include water, saline, alcohol, glycols including polyethylene glycol, oil, polysaccharides, salts, glycerol, stabilizers, emulsifiers and combinations thereof. Useful antibacterial agents include antibiotics, bacterial-static and bacterial-toxic chemicals. Agents to optimize speed of detection may increase reaction speed such as salts and buffers.

Another embodiment of the invention is directed to a method for creating a library of receptor proteins or any proteins which show variability. Receptor proteins which may be utilized in this method may be any eukaryotic or prokaryotic proteins which have variable regions including T-cell receptors such as the TcR, B-cell receptors including immunoglobulins, natural killer cell (NK) receptors, macrophage receptors and parts and combinations thereof. Briefly, a sample of biological tissue, such as normal tissue, neoplastic tissue, infected tissue, tissues containing extracellular matrix (ECM) proteins, or any abnormal tissue, is introduced to a cell population capable of producing the receptor proteins. The cell population is fixed and the cells permeabilized. The variable region mRNAs of the receptor proteins are reverse transcribed into cDNA sequences using a reverse transcriptase. The cDNA sequences are PCR amplified and linked, preferably by hybridization of complementary sequences at the terminal regions of these cDNAs. The linked sequences are PCR amplified to create a population of DNA fragments which encode the variable regions of the receptor proteins. These DNA fragments contain the variable regions linked, preferably, in a head-to-head transcriptional orientation and are cloned in-mass into expression vectors. Useful expression vectors include phages such as display phages, cosmids, viral vectors, phagemids or combinations thereof, and the vectors transformed into host organisms and the different populations of organisms expanded. The expression vectors which encode the recombinant receptor proteins are selected and the sub-population expanded. The sub-population may be subcloned into expression vectors, if necessary, which contain receptor constant region genes in-frame and the library again expanded and expressed to produce the sub-library of selected receptor proteins. Chimeric libraries can be easily created by cloning the selected variable region genes into expression vectors containing constant region genes of other proteins such as antibody constant region genes or T cell receptor genes. The selected sub-libraries can be used directly or transferred to other expression vectors before transfection into host cells. Host cells may be T cells derived from the patient which, when introduced back into the patient, express the receptor library on their surface. This type of T cell therapy can be used to stimulate an immune response to treat the same diseases as those described for antibody therapy.

Using the methods discussed above for the creation of polyclonal antibody libraries and libraries of T cell receptors, libraries of chimeric fusion proteins can be created which contain the variable regions of antibodies joined with the constant regions of T cell receptor. Such libraries may be useful for treating or preventing diseases and disorders, as described above, by stimulating or enhancing a patient's immune response. For example, antigen binding to the T cell receptor is an integral part of the immune response. By providing a chimeric antibody/TcR protein library and by transfecting this library into a patient population of T cells, the patient's own immune response may be enhanced to fight off a disease or disorder that it could not otherwise successfully overcome.

Another embodiment of the invention is directed to nucleic acid vectors which can be used to create the antigen-specific polyclonal antibody libraries and sub-libraries. These vectors comprise restriction enzyme recognition sites convenient for cloning and sequences to efficiently PCR amplify recombinant nucleic acid fragments. Suitable vectors include plasmids, phages, phagemids, display phages, cosmids, viral vectors and combinations thereof. Vectors are designed to have one or more pairs of genetic fragments, such as cDNA fragments, inserted in a head-to-head transcription orientation. Preferably, the vectors are expression vectors and may be prokaryotic, eukaryotic or combinations or parts thereof. These vectors also preferably contain transcription and translation controlling sequences such as TATA boxes, CAT boxes, ribosome binding sites, RNA polymerase initiation and termination sites, leader sequences, strong transcriptional promoters, which may be regulated, or parts or combinations thereof.

By way of example, a useful vector can be constructed as graphically depicted in FIG. 2. First, the vector backbone can be obtained from a commercially available phagemid vector such as pUC119 (United States Biochemical; Cleveland, Ohio) as shown in FIG. 2B. Two primers are used to amplify a pUC119 backbone beginning at the end of a lacZ' and ending at the beginning of lacI. The forward primer is complementary to the end of the lacZ' and has a non-hybridizing tail containing a BglII site. The reverse primer is complementary to the beginning of lacI and has a non-hybridizable tail that contains a BstEII site. After PCR amplification, this backbone is digested with BglII and BstEII and ligated with a BstEII insert (FIG. 2B). The BstEII insert is obtained as follows (FIG. 2A): First, the polylinker of pUC19 (New England BioLabs; Beverly, Mass.) is replaced with a polylinker that contains BglII-EcoRI-HindIII-BstEII, wherein each restriction site is separated by six nucleotides. Replacement is achieved by digesting pUC19 with EcoRI and HindIII, removing the overhangs with S1 nuclease, and ligating the backbone with a double-stranded synthetic linker containing the sites BglII-EcoRI-HindIII-BstEII to generate pUC19 modified (pUC19mod). (Note that pUC19 is being used only to provide a polylinker containing restriction enzyme sites. Any other vector, existing or easily created that contains a polylinker with appropriate restriction sites, could be used instead.) A Cκ gene is reverse transcribed from RNA derived from human leukocytes, and amplified by PCR using a reverse primer which comprises a 5' non-hybridizing tail containing a BstEII restriction site, a translation termination site (stop site) and an XbaI site, and a forward primer which comprises a 5' non-hybridizing tail containing a HindIII restriction site. This PCR product is digested with BstEII and HindIII and ligated with a BstEII-HindIII pUC19mod backbone to generate pUC19-Cκ. An EcoRI-BglII DNA fragment containing the human γ1 CH1 gene tethered to the gIII gene segment that encodes a fragment of the cpIII phage coat protein (amino acids 198–407) is synthesized. Briefly, a cpIII coat protein gene fragment is amplified from an M13 vector such as M13mp18 (New England BioLabs; Beverly Mass.) using a reverse primer complementary to the end sequence of the cpIII fragment, but with a 5' non-hybridizing tail that contains a BglII site, a translation termination site (stop site) and a NheI site. The forward primer for the cpIII fragment amplification is complementary to cpIII and has a 5' non-hybridizing tail which contains sequence complementary to the end of the CH1 gene and a SpeI site. A human CH1 gene is reverse transcribed from RNA derived from human leukocytes and PCR amplified using a reverse primer complementary to the end of the γ1 CH1 gene with a 5' non-hybridizing tail that contains a SpeI site. The forward primer is complementary to the beginning of the CH1 gene with a 5' non-hybridizing tail that contains an EcoRI site. Because the forward and reverse primers contain complementary ends, the cpIII and CH1 PCR products are tethered by overlap extension PCR using the cpIII reverse primer and the CH1 forward primer. The resulting PCR product is cut with EcoRI and BglII and ligated with an EcoRI-BglII backbone derived from pUC19-Cκ, to generate pUC19-Cκ-CH1. The BglII-BstEII insert is removed and ligated with the BglII-BstEII backbone derived from pUC119 to generate the phh3hu-like vector, pUC119-Cκ-CH1 (FIG. 2B).

Figure 2A:
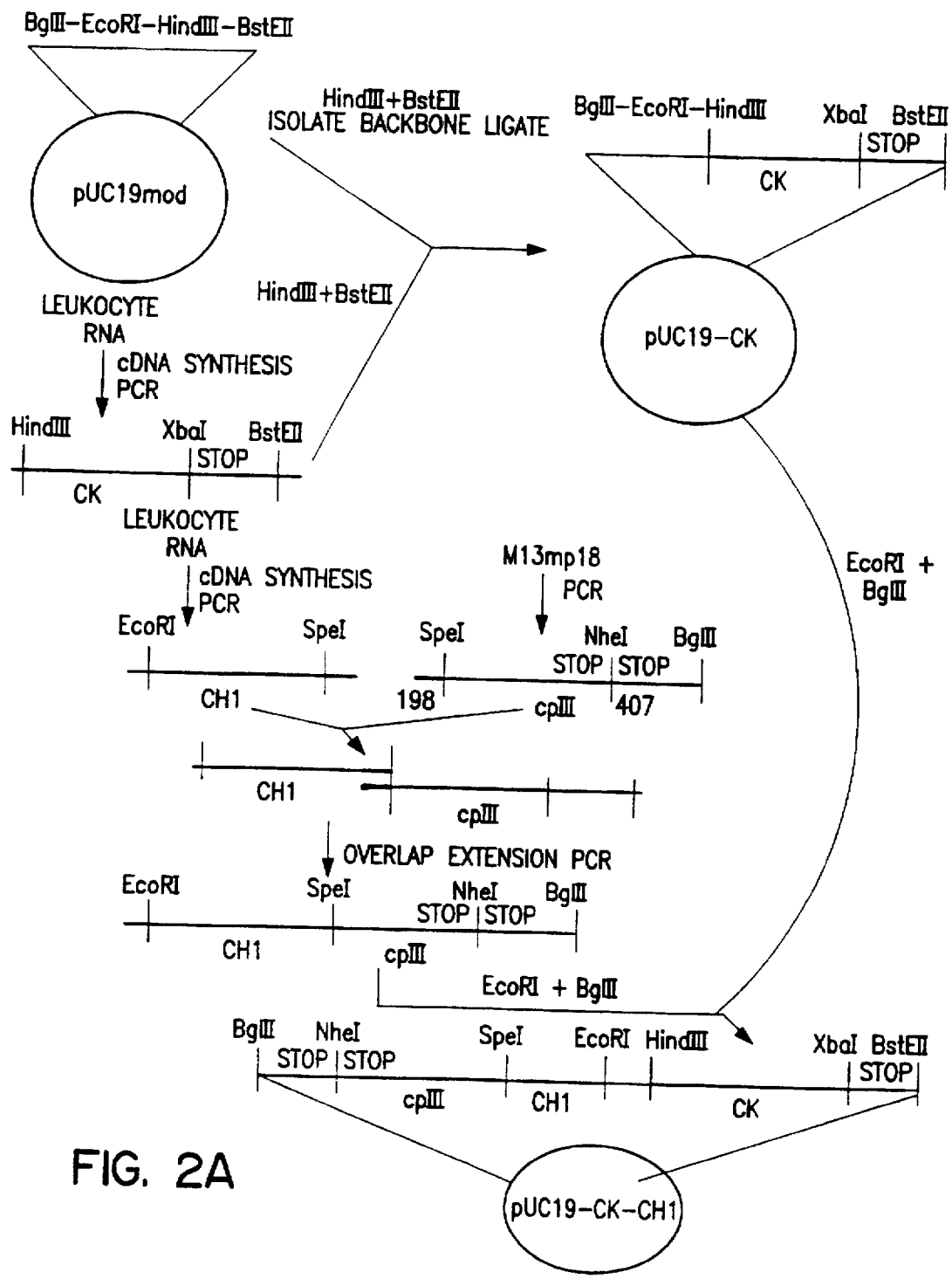
FIGS. 2A-2D. Diagrammatic representation of the construction of (FIG. 2A) pUC19-Cκ-CH1, (FIG. 2B) pUC119-Cκ-CH1, (FIG. 2C) plPPl2, and (FIG. 2D) pJS.
Figure 2B:
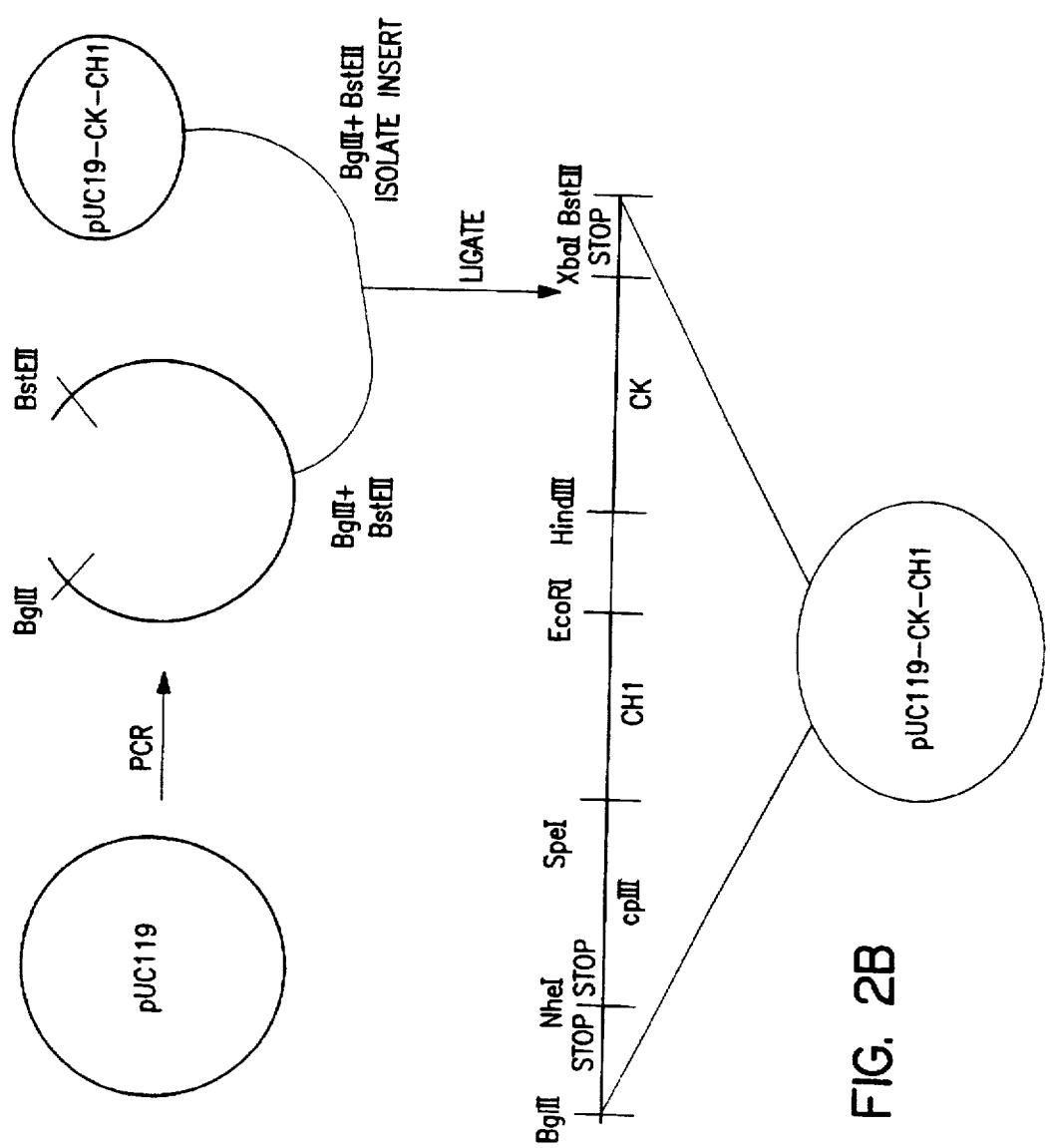
Figure 2C:
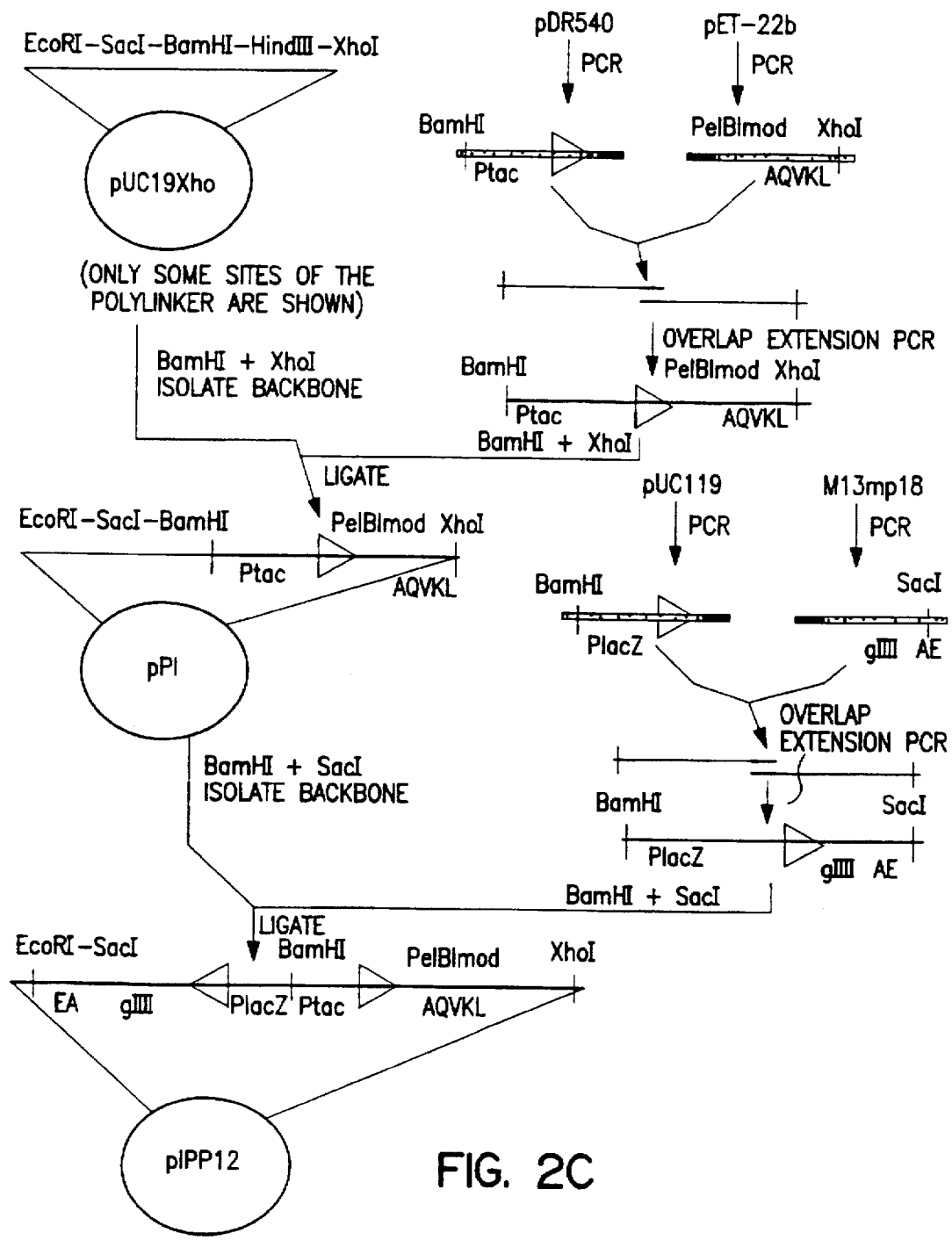
Figure 2D:
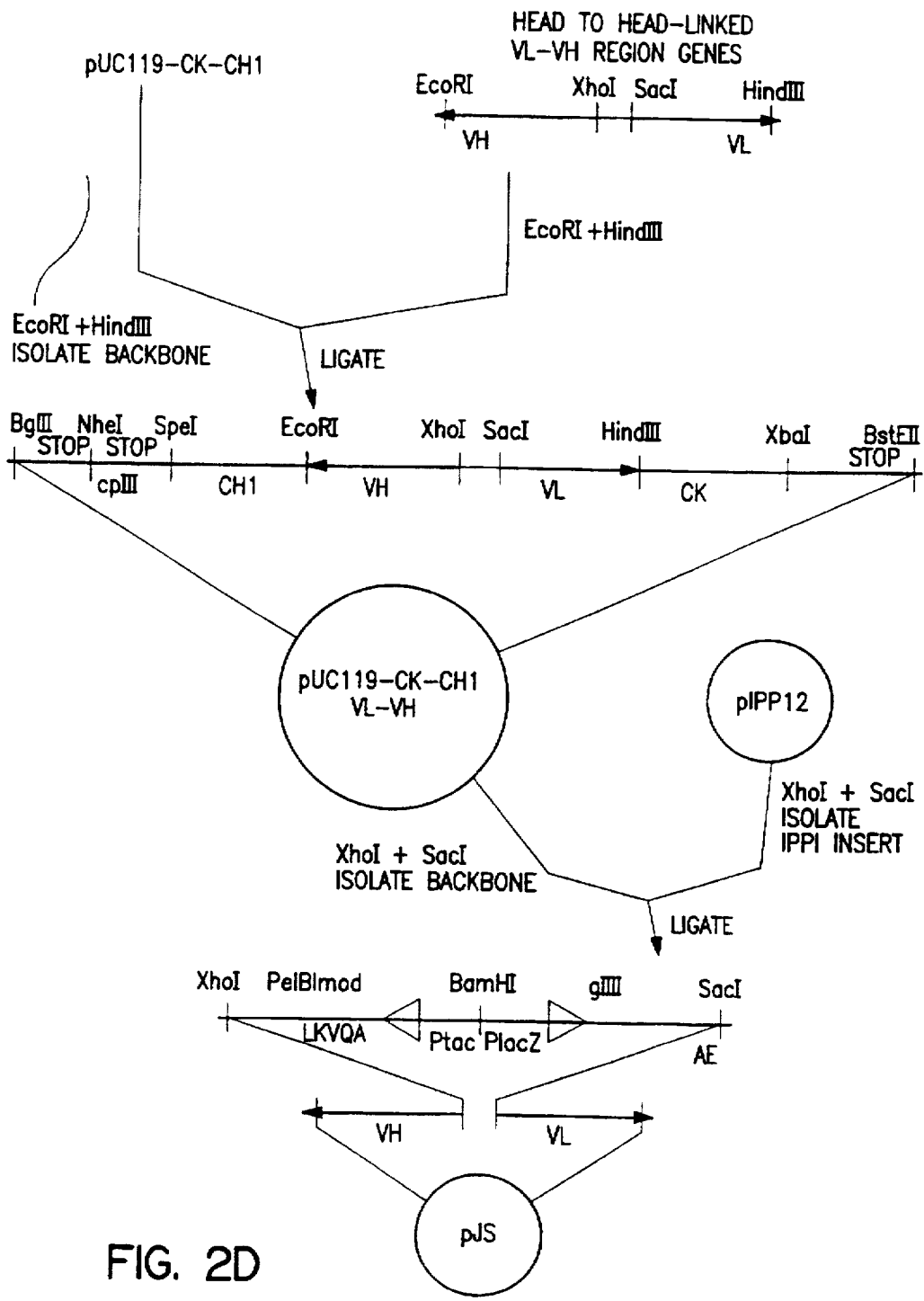

An IPPI-type cassette can be easily generated as well (FIG. 2C). A BamHI-XhoI fragment is assembled from the tac promoter (Ptac) and pelB leader sequences. The pelB leader sequence is obtained by PCR amplification from vector pET-22b (Novagen, Inc.; Madison, Wis.) using a forward primer, and a reverse primer with a 5' non-hybridizing tail that contains a XhoI site and codons for LKVQA (SEQ ID NO: 10). The Ptac sequence is obtained by PCR amplification from vector pDR540 (Pharmacia Biotech; Piscataway, N.J.) using a forward primer with a 5' non-hybridizing tail that contains a BamHI site and a reverse primer with a 5' non-hybridizing tail that is complementary to the beginning sequence of the pelB leader in pET-22b. The pelB leader and Ptac PCR products can hybridize via their complementary ends and are tethered by overlap extension PCR using the BamHI and XhoI containing primers. The resulting PCR product is digested with XhoI and BamHI and ligated with a XhoI-BamHI backbone derived from pUC19Xho, to generate pPI. (The pUC19Xho backbone is formed by digesting pUC19 with HindIII, filling in the overhangs with Klenow, and ligating the backbone with an XhoI linker.) A BamHI-SacI fragment is assembled from the lacZ promoter (PlacZ) and gIII leader sequence of the M13 cpIII coat protein. The gIII leader sequence is obtained by PCR amplification from M13mp18 using a forward primer and a reverse primer that has a 5' non-hybridizing tail containing a SacI site and the codons for EA. The PlacZ sequence is obtained by PCR amplification from pUC119 using a forward primer with a 5' non-hybridizing tail that contains a BamHI site and a reverse primer with a 5' non-hybridizing tail that is complementary to the beginning sequence of the gIII leader. The gIII leader and PlacZ PCR products can hybridize through their complementary ends and are tethered by overlap extension PCR using the BamHI and SacI containing end primers. The resulting PCR product is digested with SacI and BamHI and ligated with a SacI-BamHI backbone derived from pP1 to generate the plPP1-like vector plPP12. As shown in FIG. 2D, head-to-head linked $V_H$-$V_L$ region genes can be inserted into vector pUC119-Cκ-CH1. The resulting vectors can be opened with XhoI and SacI to insert an lPP1 cassette from vector plPP12 to generate pJS.

Another embodiment of the invention is directed to a method for the transfer of a library of nucleic acid fragments between different vectors without significant loss of library diversity. The library may be a library of cDNA fragments, genomic DNA fragments, recombinant nucleic acids, RNA or a combination thereof. The fragments are inserted into first vectors in a head-to-head transcriptional orientation. Insertion may be by ligation of the nucleic acids into vectors opened by restriction enzyme cleavage. Fragments may be modified prior to insertion such as by the addition of linkers and restriction enzyme or other sites, or by attachment to additional coding sequences. The first and second vectors may be prokaryotic or eukaryotic vectors and are preferably expression vectors. The inserted sequences are obtained from the first vectors and reinserted into second vectors without significant loss of library diversity. The fragments may be obtained by cleaving the recombinant first vectors, in bulk, with appropriate restriction enzymes. Alternatively, the sequences of the fragments may be obtained by PCR amplification of the inserted sequences. Reinsertion is by ligation of the sequences into the second vectors, but the sequences may be modified if desired before ligation as described. The overall library diversity comprises upwards of at least ten different fragments, preferably 100 different fragments, more preferably 1,000 different fragments, even more preferably at least 10,000 different fragments and possibly much more such as $10^5$, $10^6$, $10^7$, $10^8$ and $10^9$ different fragments. After transfer, library diversity, as may be measured by analyzing the resulting recombinants, is expected to be reduced by less than 90%, preferably by less than 50%, more preferably by less than 10%, even more preferably by less than 1% and still more preferably by less than 0.1%, although this may be more dependant upon the particular type of library being created.

The following examples illustrate embodiments of the invention, but should not be viewed as limiting the scope of the invention.

EXAMPLES

Example 1

In vivo and In vitro Preparation of Tumor Samples

Pathological discards of human tumors and normal tissues were obtained from Surgical Pathology at the Boston University Medical Center. Of the tumors processed, three were ovarian carcinomas, two were adenocarcinomas of the uterus, one was a mesothelioma of the peritoneum, and one was from the oral floor of a mouth tumor. Two pieces of the tumor tissue and two pieces of any available normal tissue were snap frozen in OCT (polyvinyl alcohol, benzalkonium chloride, polyethylene glycol, all in distilled $H_2O$; Miles Laboratories; Kankakee, Ill.) for subsequent preparation of frozen (cryostat) sections. If enough normal tissue was available, some samples were snap frozen without OCT for subsequent preparation of membranes for later antibody absorption.

Tumor tissues were minced into about 1 mm$^3$ pieces and digested for 45 minutes at 37° C. with a mixture of enzymes consisting of 1 mg/ml collagenase type IA, 1 mg/ml collagenase type IV, 200 pg/ml DNase, and 100 units/ml hyaluronidase in Iscove's Modified Dulbecco's Medium (IMDM). The mixture was filtered through nitex to remove undigested pieces and to collect cell suspensions which were used to inject subcutaneously (s.c.) into BALB/c nude mice to develop tumors, to set up in explant cultures in D-Val supplemented media, and to freeze as aliquots in 90% human serum/10% dimethylsulfoxide (DMSO).

Suspended cells were washed with IMDM and loaded onto Percoll/phosphate buffered saline (PBS) step gradients. Tumor cells were isolated from the interface between 1.07 g/ml Percoll and the PBS. The isolated tumor cells were injected into BALB/c mice i.p. to obtain anti-tumor antibodies, injected s.c. into BALB/c nude mice to develop tumors, set up in culture in D-Val medium supplemented with 30% of a dialyzed mixture of equal parts of human serum, fetal bovine serum (FBS) and rat fibroblast culture cell supernatant, to establish cell lines, and frozen in aliquots with 90% human serum/10% DMSO for later use.

One of the ovarian tumors processed was diagnosed as a moderately differentiated adenocarcinoma. The following specimens were obtained from the patient on the day of surgery; a tumor sample from the ovary, a lymph node metastasis, and normal myometrium, endometrium, and small intestine. The tumor and normal tissue samples were processed as described above. The tumor cell-enriched fraction, isolated on the Percoll gradient, consisted primarily of small clumps of large cells and a direct cell count could not be obtained. Cell numbers were estimated after centrifugation, based on experience with similar size cells. Recovery was estimated at $2 \times 10^8$ cells from the ovarian tumor. A subsequent cytospin preparation of the cells was analyzed and determined to contain mostly tumor cells. Four BALB/c mice were each injected i.p. with 0.25 ml of this cell suspension in IMDM (estimated at $10^7$ cells per mouse) to produce anti-tumor antibodies.

One nude mouse was injected s.c. with 0.2 ml of minced tumor in IMDM derived from the ovary. Another nude mouse was injected s.c. with 0.2 ml of minced tumor derived from the lymph node. Both nude mice developed subcutaneous tumors. The tumors were evident 15–18 days after the injection. The mouse injected with the ovary-derived tumor was sacrificed 1 month post injection when the tumor was about 1.5 cm×1 cm×0.5 cm. An analysis of a cytospin preparation of cells isolated from its tumor by Percoll gradient centrifugation showed it to be of human origin and of the same type as the original ovarian tumor. This tumor could be further propagated in both nude and SCID mice by s.c. injection of either fresh minced tumor pieces or of tumor pieces that had been frozen in 90% human serum/10% DMSO and thawed for injection.

The tumor that developed in the nude mouse injected with tumor pieces derived from the lymph node metastasis was further processed. After snap-freezing a sample in liquid nitrogen, the tumor was minced into 1 cm pieces. Half of the minced pieces were frozen in aliquots of about 0.4 ml (packed tumor pieces) in 90% human serum/10% DMSO, and stored in liquid nitrogen. The other half was used to prepare a tumor cell suspension by Percoll density gradient centrifugation as described above. The recovered cells were frozen in two aliquots of about $4 \times 10^7$ cells, each in 90% human serum/10% DMSO and stored in liquid nitrogen. Percoll isolated cell suspensions of the OC2 tumor were used to generate i.p. and s.c. tumors in a nude mouse. OC2 tumors in both BALB/c nude and SCID mice were propagated by i.p. injection of tumor pieces (0.25 ml). OC2 tumor tissue could be propagated in immunodeficient mice and both subcutaneous and intraperitoneal tumors developed in a nude and a SCID mouse.

Because of the successful propagation of the OC2 tumor in both nude and SCID mice, a 10 cc heparinized blood sample was obtained from the OC2 patient. The leukocyte fraction ($1.4 \times 10^7$ cells) was isolated, frozen in 90% human serum/10% DMSO and stored in liquid nitrogen. Additional blood samples were also obtained from the patient. The normal myometrium sample obtained from the patient on the day of surgery and frozen in liquid nitrogen was processed to obtain preparations of membranes. The frozen tissue was ground with a mortar and pestle in liquid nitrogen, homogenized in a buffer containing the protease inhibitors leupeptin, aprotinin, pepstatin, and PMSF, and centrifuged for 10 minutes at 1,200×g to remove cell debris. Membrane-containing pellets were obtained by centrifugation at 150,000×g for 90 min. and stored at −80° C. in aliquots containing 10% glycerol.

The OC2 carcinoma was propagated in both BALB/c nude and SCID mice, by s.c. or i.p. injection of either fresh or previously frozen minced tumor pieces. In addition to a constant supply of fresh human tumor propagated in the nude or SCID mice, frozen aliquots of minced tumor and of Percoll gradient-isolated tumor cells derived from the first passage of the OC2 lymph node metastasis through a nude mouse were prepared. Cells and tissue pieces obtained directly from the patient were frozen in 90% human serum/10% DMSO and stored in liquid nitrogen. This included fourteen aliquots of an estimated $10^7$ cells each of Percoll-separated OC2 tumor cells derived from the patient's ovary, three aliquots of about 0.75 ml each of minced OC2 lymph node metastasis from the patient, five aliquots each of $2.8 \times 10^6$ patient PBLs and samples of the ovarian tumor. The lymph node metastasis, the myometrium, endometrium, and small intestine were snap frozen in liquid nitrogen with or without OCT, and stored at −80° C.

Example 2

Generation and Testing of OC2 Immune Mice Antisera

Four BALB/c mice were immunized once i.p. with about $10^7$ OC2 cells derived from the ovary. The mice were boosted i.p. on day 30 with about $5 \times 10^6$ OC2 tumor cells from the original preparation that had been frozen in 90% human serum/10% DMSO, stored in liquid nitrogen, and thawed and washed before use. Antisera were obtained on days 12 and 30 post primary immunization and on day 11 post secondary immunization. Additional boosts can be administered to the mice, both i.p. and i.v., until no further increase in response is obtained. Reactivity of the antisera with the OC2 tumor cells, compared to the reactivity of pre-immune sera, is determined by solid phase ELISA using plates coated with OC2 tumor membrane preparations and alkaline phosphatase labeled goat anti-mouse immunoglobulin and nitro blue tetrazolium (NBT) plus indolyl-phosphate (BCIP) substrate (Promega; Madison, Wis.) as developing reagents.

The reactivity of the antisera with four micron cryostat sections of the OC2 tumor can be determined by immunohistochemistry. Acetone-fixed samples are treated with 0.3% $H_2O_2$ in methanol to destroy endogenous peroxidase activity then rehydrated in PBS/1% FBS. They are then incubated with the antisera for about 30 to 60 minutes at room temperature, rinsed, and incubated with biotinylated rabbit anti-mouse Ig. Stains are developed with avidin-horseradish peroxidase and diaminobenzidine. Sections are counter stained with methyl green.

Example 3

Generation of Bacterial and Mammalian Expression Vectors

Expression vectors, both mammalian and bacterial, were prepared in which linked combinations of $V_H$ and $V_L$ regions genes could be transferred, in bulk, from the B cells in which they are expressed into bacterial expression vectors, and without losing the combinations, into mammalian expression vectors. The H and L chains, in both vectors, are arranged in opposite transcriptional orientations with head-to-head promoters. In this way the V region gene combination could be transferred as a unit between vectors. Furthermore, as long as all vectors are circular, vectors can be opened by restriction enzymes between the $V_H$ and $V_L$ region genes to insert intervening DNA fragments such as promoters, without loss of the $V_H$-$V_L$ combination, which remains on the same piece of DNA.

Chimeric proteins can be expressed on the surface of filamentous (M13) phage if fused to a phage coat protein such as cpIII or cpVIII. The circular phagemid expression vector pComb3, which contains an insertable site in frame with cpIII was utilized for these studies, although other similar, commonly available vectors can be used. A pComb3 phagemid vector DNA was created encoding an Fd portion ($V_H$ and $C_{H1}$ domains) of an antibody. The genetic region encoding the antibody portion was fused to the gene gIII encoding the carboxyl terminus end of cpIII (FIG. 3). The vector is circular and digestion with SpeI and NheI, which produces compatible cohesive ends, results in the removal of the gIII coat protein fragment, and after religation, allows for the production of free Fab. Phage-display libraries of $10^7$ members can be obtained after co-infection of XLI-Blue *E. coli* with helper phage, and selected for antigen binding by panning on antigen-coated surfaces. Genes encoding the selected Fab fragments are carried in the phage particles and thus, immediately available for cloning and sequencing.

The pComb3 vector also encodes free L chain ($V_L$ and $C_L$-kappa domains) which associates with the coat protein-fused Fd region to form Fab fragments displayed on the surface of the phage. The Fd-cpIII fusion protein and the L chain are expressed from their own (lacZ) promoters in head-to-tail transcriptional orientations. To obtain an array of phage expressing high affinity antibodies directed against a variety of antigens such as those on the surface of a tumor cell, it is more efficient to have the H and L chain combinations generated in vivo in response to immunization.

To obtain a bacterial vector in which the $V_H$ and $V_L$ region genes could be arranged in opposite transcriptional orientations, the pComb3 phage display vector was modified. This modified pComb3 vector (phh3, FIG. 3b) contains the lacZ and the tac promoters in head-to-head transcriptional orientations, driving transcription of the mouse kappa and Fd genes respectively. The $C_{H1}$ domain of the Fd gene is derived from $IgG_{2b}$. Although the leader sequences for both chains have the pelB leader amino acid sequence, the nucleotide sequences differ at many positions. This precaution was taken to guard against deletions. The integrity of this phagemid vector in both double-stranded and single-stranded forms was verified by diagnostic restriction enzyme analysis, by sequencing, and by PCR amplification of specific segments.

The DNA segment containing the head-to-head bacterial promoter and leader sequences of phh3, a bacterial IPP1 cassette, was generated by subcloning into pBluescript II KS (Stratagene; La Jolla, Calif.), to generate pIPP1 (FIG. 3c). The phh3 vector was modified by replacement of the variable region genes and the leader and promoter sequences with a stretch of irrelevant DNA to produce phh3mu containing the murine Cκ and $\gamma_{2b}$ CH1 genes (FIG. 3d). An additional bidirectional phage display vector containing the human Cκ and $\gamma_1$ CH1 genes (phh3hu; FIG. 3d) was derived from phh3mu by replacement of the murine C genes with human C genes.

Both phh3mu and phh3hu are useful for cloning of linked $V_L$–$V_H$ pairs in a head-to-head transcriptional orientation. These circular vectors can be opened between the amino termini of the $V_L$ and $V_H$ region genes to insert the IPP1 cassette derived from pIPP1 and generate a bidirectional phage display library. As depicted in FIG. 4c, $V_L$–$V_H$ pairs, linked in a head-to-head transcriptional orientation can be easily transferred, in bulk, between a circular bidirectional phage display vector and a circular mammalian expression vector. The transfer requires opening the vector between the $V_L$ and $V_H$ amino termini and exchanging cassettes containing either prokaryotic or mammalian promoter and leader sequences. The $V_L$–$V_H$ pairs including the IPP1 cassettes are lifted from one vector, by PCR, and inserted into another vector. For insertion into the mammalian vector, the nonhybridizing tails of the PCR primers contain splice sites (ss=splice site; FIG. 3c).

A murine dual vector, pMDV (FIG. 4a), capable of expressing a mouse IgG$_{2b}$ H chain and a mouse kappa L chain was engineered and used to express IgG$_{2b}$ antibodies by transfection into the null hybridoma cell line Sp2/0-Ag14 which produces no endogenous H or L chain. The IgG$_{2b}$ C region gene is replaced with the IgG$_{2a}$ C region gene by enzymatic manipulations as described in *Molecular Cloning: A Laboratory Manual* (J. Sambrook et al. editors, Cold Spring Harbor Laboratory; Cold Spring Harbor, N.Y. 1989). The murine dual vector can also be modified by replacing the murine Cγ$_{2b}$ and Cκ genes with the human Cγ$_1$ and Cκ genes respectively, to generate the chimeric dual vector (pCDV) shown in FIG. 4b. The Eco gpt selectable marker confers on mammalian cells resistance to mycophenolic acid when xanthine is present in the medium.

Example 4

Cell Fixation and Permeabilization

Cells were fixed basically as described by M. J. Embleton et al. (Nuc. Acids Res. 20:3831–37, 1992) with minor modifications. Cells at 3–5×10$^7$, in a 50 ml conical tube (Costar; Cambridge, Mass.) were washed three times in 10 mls of PBS, pH 7.2, at room temperature. The cell pellet was resuspended in 1.0 ml of 150 mM NaCl, followed with 1.0 ml of ice cold 20% formaldehyde (Sigma Chemical; St. Louis, Mo.)/150 mM NaCl was added dropwise with gentle vortexing. Cells were kept on ice and vortexed at 10 minute intervals for a total of one hour, then washed three times with ice cold PBS at 350×g for three minutes at 4° C. The tube was tapped to disperse the pellet between washes. The pellet was resuspended in 1.0 ml of 0.5% NP-40 (Sigma Chemical; St. Louis, Mo.) in water. The cells were kept on ice for one hour with occasional vortexing, then transferred to a microfuge tube and centrifuged at 14,000 rpm at 4° C. for 3 minutes. Three washes with ice cold PBS and one wash with ice cold PBS/100 mM glycine followed. Between washes, the pellet was dispersed by rigorous tapping of the microfuge. Cells were resuspended in PBS/100 mM glycine with a micropipettor to disperse the cell pellet and to remove visible cell clumps. Aliquots of 10$^6$ cells in PBS/100 mM glycine were frozen on dry ice and stored at −80° C. for up to three weeks.

Example 5

In-Cell Linking of H and L Chain V Region Genes

An in-cell PCR procedure was established in which $V_H$ and $V_L$ region cDNAs were synthesized in situ in a population of fixed/permeabilized cells. Two transfectant cell lines were generated, one cell line produces a mouse IgG$_{2b}$ (κ) antibody specific for the hapten p-azophenylarsonate (Ars; J. Sharon et al., J. Immunol. 142:596–601, 1989). The other cell line produces a chimeric IgG$_{2b}$(κ) antibody that is identical to the anti-Ars antibody at both the amino acid and nucleotide levels, except in the complementarity determining regions (CDRs), which are derived from an anti-dextran antibody. These two cell lines were used because primers for cDNA synthesis and PCR, which do not include the CDRs, have the same complementarity to the H and L genes of both cell lines, yet the resulting linked $V_H$–$V_L$ combinations could be distinguished by sequencing into the CDRs.

cDNA synthesis and PCR amplifications in fixed/permeabilized cells was performed basically as described by M. J. Embleton et al. (Nuc. Acids Res. 20:3831–37, 1992) with minor modifications. Two×10$^6$ fixed/permeabilized cells were washed once with water and used in a 50 ul reaction for cDNA synthesis. Forty units of SuperScript reverse transcriptase (Gibco/BRL; Grand Island, N.Y.) first strand buffer (Gibco/BRL; Grand Island, N.Y.) and 25 pmoles each of the forward primers 3A-CL (SEQ ID NO: 1) and 1A-CH1 (SEQ ID NO: 2) (Operon Technologies; Alameda, Calif.) were used. Following cDNA synthesis, cells were microfuged (14,000 rpm for 3 minutes at 4° C.), washed in 200 ul PBS/100 mM glycine and resuspended in 10 ul of the same buffer. PCRs were performed with the AmpliTaq DNA polymerase kit (Perkin-Elmer Cetus; Norwalk, Conn.) in a DNA Thermal Cycler 480 (Perkin-Elmer Cetus; Norwalk, Conn.) for 30 cycles. Each cycle consisted of 30 seconds at 95° C., 30 seconds at 65° C., and 30 seconds at 72° C. The final concentration of MgCl$_2$ was 2.5 mM. A 20 ul PCR control that yields a 1.2 kilobasepair product was included.

In the first PCR, 10 pmoles each of the linking primers 4L (SEQ ID NO: 3) and 2H (SEQ ID NO: 4) along with 25 pmoles each of the forward primers 3A-CL (SEQ ID NO: 1) and 1A-CH1 (SEQ ID NO: 2) were used.

Forward Primers:

|  | 127 | 118 |
|---|---|---|
| 3A-CL (as) | 5'-GA TGT TAA CTG CTC ACT GGA TGG TGG G-3' | (SEQ ID NO 1) |
|  | 135 | 124 |
| 1A-CH1 (as) | 5'-C AGT TGT ATC TCC ACA CCC AGG GGC CAG-3' |  |
|  |  | (SEQ ID NO 2) |

-continued

Linking Primers:

| | Linker | 1SacI |
|---|---|---|
| 4L (s) | 5'-CAG TCA GTC AGT CAG TCA GTC AGT CAG TCA GAG CTC | |
| | 13 | |
| | CAG ATG ACA CAG ACT ACA TCC TCC CTG TCT GCC-3' | |
| | | (SEQ ID NO 3) |

| | Linker | |
|---|---|---|
| 2H (s) | 5'-CTG ACT GAC TGA CTG ACT GAC TGA CTG ACT GAG GTT | |
| | 1    XhoI    14 | |
| | CAG CTT CTC GAG TCT GGA GCT GAG CTG GTG AGG GC-3' | |
| | | (SEQ ID NO 4) |

Nested Primers:

| | 117 C$_K$ | EcoRI | Splice Site | 108 |
|---|---|---|---|---|
| 3L (as) | 5'-GAT GGA TAC AGT TGG GAA TTC ATT CTA CTT ACG TTT | | | |
| | J$_K$1  100 | | | |
| | GAT TTC CAG CTT GGT GCC TCC-3' | | | (SEQ ID NO 5) |
| | 123  C$_{H1}$ | HindIII | Splice Site | 108 |
| 1H (as) | 5'-GG ATA GAC TGA TGG AAG CTT GGA CTC ACC TGA GGA | | | |
| | J$_{H2}$  106 | | | |
| | GAC TGT GAG AGT GGT GCC-3 | | | (SEQ ID NO 6) |

Sequencing Primer:

| | 64 | 57 | |
|---|---|---|---|
| V$_K$F3REV(as) | 5'-GCC ACT GAA CCT TGA TGG GAC TCC-3' | | (SEQ ID NO 7) |

Promoter/Leader Primers:

| | 7  SacI | -3 | |
|---|---|---|---|
| V$_K$Sac (as) | 5'-GTG TCA TCT GGA GCT CAC ATC TGG-3' | | (SEQ ID NO 8) |
| | 13 HindIII | XhoI | |
| VHH3X (as) | 5'-CCT CAC CAG CTA AGC TTC AGA TTC AGA CTC GAG AAG | | |
| | 2 | | |
| | CTG AAC-3' | | (SEQ ID NO 9) |

Figure 6:
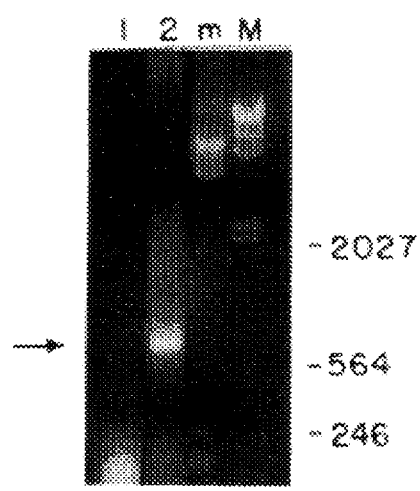
FIG. 6. Agarose gel analysis of PCR products.

Following the first PCR, cells were microfuged and the supernatant collected. For the second PCR, after two washes of 200 ul PBS/100 mM glycine, 25 pmoles each of the nested primers 3L and 1H were added. Upon completion of 30 cycles as before, the cells were microfuged and the supernatants collected. The reaction products obtained after the first and second PCRs are shown in FIG. 6. A band of 777 bp corresponding to the linked V$_H$–V$_L$ combination (indicated by an arrow) was observed after the second PCR. The products obtained as first and second PCR products are shown in lanes 1 and 2, respectively. m and M are a 123 bp ladder and a Hind III digest of kappa phage DNA, respectively, with the sizes in basepairs (bp) of some of the bands indicated. The band observed was the correct size expected for the V$_H$–V$_L$ combination. This band was gel-purified and cloned, after digestion with EcoRI and HindIII, into the EcoRI-HindIII sites of M13mp19.

Figure 5:
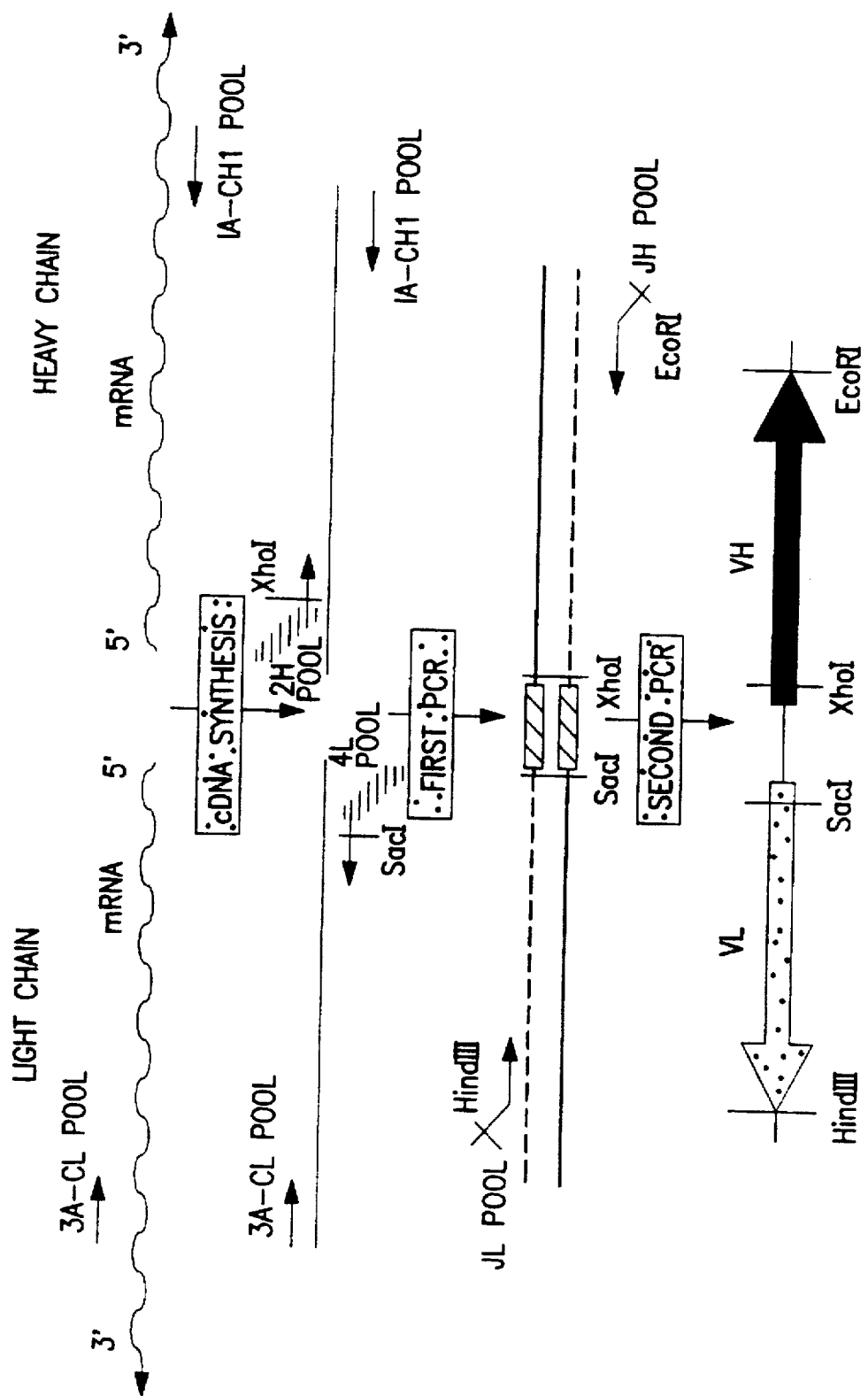
FIG. 5. Schematic representation of cDNA synthesis and PCR reactions.

A schematic representation of the in-cell reverse-transcriptase and PCR reactions, and of the products obtained is shown in FIG. 5. After cDNA synthesis using primers 1A-CH1 (SEQ ID NO: 2) and 3A-CL (SEQ ID NO: 1) (both anti-sense), complementary to the beginning of the C$_{H1}$ and CK genes for the H and L chain mRNAs respectively, the same primers plus two linking primers, 2H and 4L (SEQ ID NO: 3), were used in a first PCR reaction. In addition to providing a way to link the V$_H$–V$_L$ combination within cells, the linking primers introduce restriction sites (XhoI and SacI) for the subsequent cloning of promoter sequences between V$_H$ and V$_L$. Primer 2H (SEQ ID NO: 4) hybridizes to the beginning of the V$_H$ sequence including part of the leader sequence, has a Xho I restriction enzyme site corresponding to amino acid positions 5 and 6 of the V$_H$ region, and contains a 30 nucleotide-long tail of random sequence. Primer 4L (SEQ ID NO: 3) hybridizes to the beginning of the VK sequence including part of the leader sequence, has a Sac I restriction site corresponding to amino acids 1 and 2 of the VK region, and contains a 30 nucleotide-long tail which is the reverse complement of the tail of primer 2H (SEQ ID NO: 4).

Because the tails of primers 2H (SEQ ID NO: 4) and 4L (SEQ ID NO: 3) are complementary, the V$_H$ and V$_L$ amplified fragments were linked during PCR by overlap extension. After washing the cells, to remove extracellular unincorporated primers and any PCR products that may have leaked out of the cells, a second PCR was set up using nested primers 1H (SEQ ID NO: 6) and 3L (SEQ ID NO: 5), both anti-sense and not overlapping with primers 1A-CH1 (SEQ ID NO: 2) and 3A-CL (SEQ ID NO: 1). Primer 1H (SEQ ID NO: 6) is complementary to the very beginning of the IgG$\gamma_{2b}$ C$_{H1}$ domain and to part of JH2. In addition, it contains a Hind III restriction site and a splice site. Primer 3L (SEQ ID NO: 5) is complementary to the very beginning of the CK domain and to part of JK1. It contains an EcoR I restriction site and a splice site. The splice sites and the restriction sites in primers 1H (SEQ ID NO: 6) and 3L (SEQ ID NO: 5) are intended to allow the subsequent cloning of the linked V$_H$–V$_L$ combinations into the dual mammalian expression vector shown in FIG. 4a.

Example 6

Figure 7:
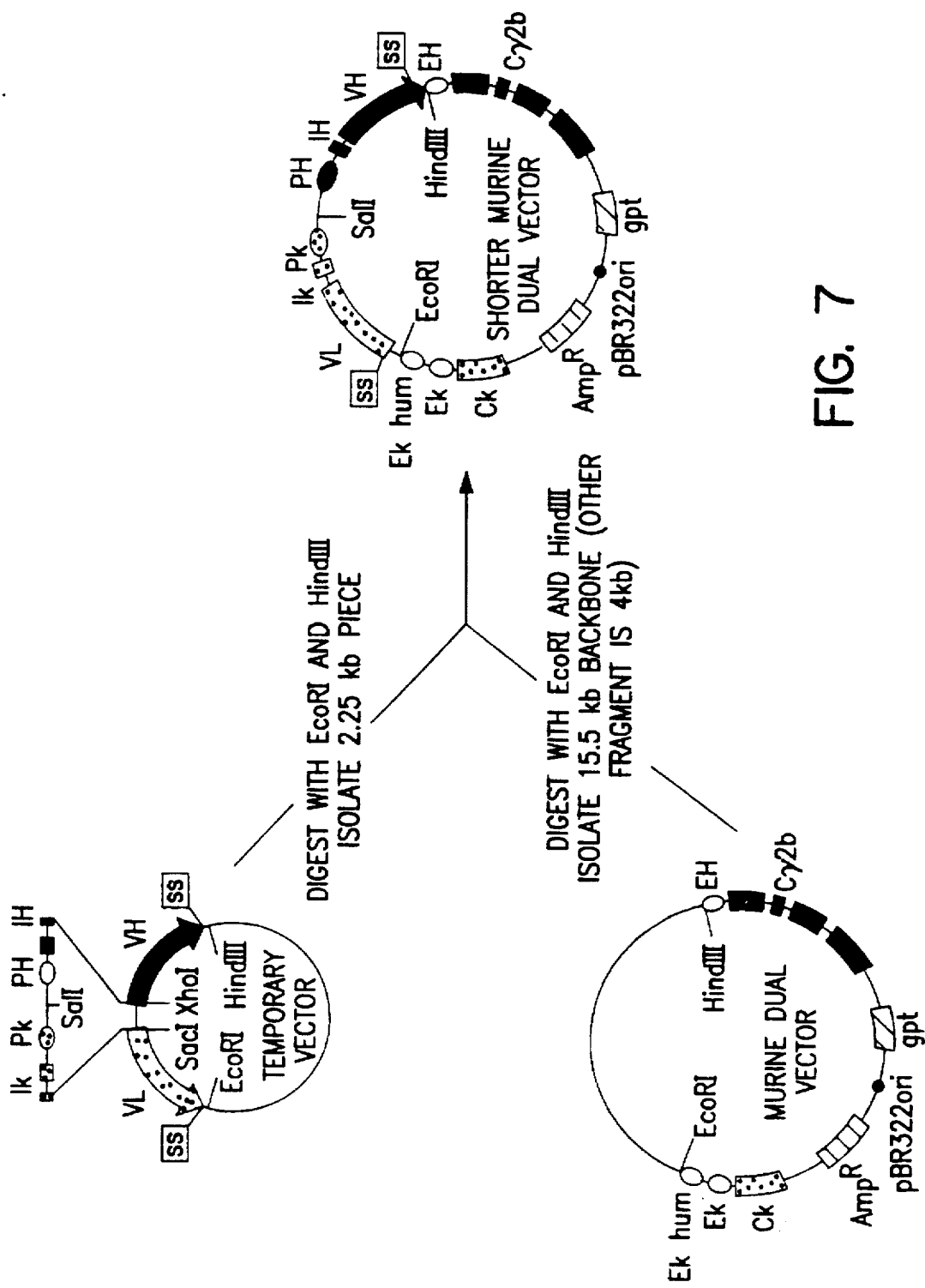
FIG. 7. Transfer of in-cell linked $V_H-V_L$ combinations to a murine expression vector.

Generation of Intact IgG Antibodies After In-Cell cDNA Synthesis and PCR Amplification To determine whether in-cell amplified V$_H$–V$_L$ combinations can be expressed as IgG antibodies in myeloma or hybridoma cells, head-to-head mammalian promoters were provided (FIG. 7). A clone containing a linked V$_H$–V$_L$ combination, encoding the V regions of the anti-Ars antibody was digested with XhoI and SacI and ligated with a XhoI-SacI DNA fragment containing an H chain promoter, a leader sequence, and DNA encoding the first four amino acids of the mature H chain, in head-to-head orientation to a kappa chain promoter and leader sequence. A 2.25 kb EcoRI-HindIII DNA fragment encompassing the promoters and the V region genes was isolated from the resulting vector, and ligated into the EcoRI-HindIII backbone derived from the IgG$_{2b}$ murine dual vector. The resulting expression vector (FIG. 7) was transfected into Sp2/0-Ag14 null hybridoma cells by electroporation.

Transfectants showed production of intact IgG antibodies as determined by Western blot analysis of their supernatants (FIG. 8a) performed as described by H. Towbin et al. (Proc. Natl. Acad. Sci. USA 76:4350–54, 1979). The position of the 150 KDa IgG product is indicated by an arrow. The positions of molecular weight markers in KDa are indicated as well as: E=the experimental transfectant derived from the in-cell linked $V_H$-$V_L$ combination; –C=negative control (parental Sp2/0-Ag14 cell line); M=pre-stained molecular weight markers; +C, positive control (an anti-Ars IgG$_{2b}$ transfectant); –A=a transfectant producing a mutant IgG$_{2b}$ antibody which has lost Ars-binding. The transfectants bound to Ars as assessed by solid phase enzyme linked immunoassay (ELISA) using Ars-BSA coated plates and alkaline phosphatase-labeled goat anti-mouse IgG (Fc specific, FIG. 8b) in the ProtoBlot system (Promega, Madison, Wis.).

Figure 9A:
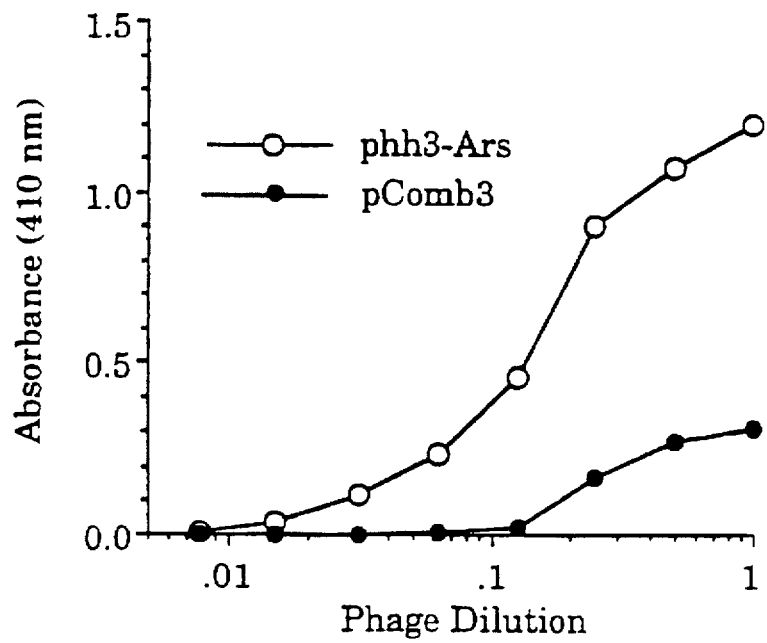
FIGS. 9A and 9B. Analysis of phage binding to Ars-BSA by (FIG. 9A) direct-binding ELISA, and (FIG. 9B) inhibition ELISA.
Figure 9B:
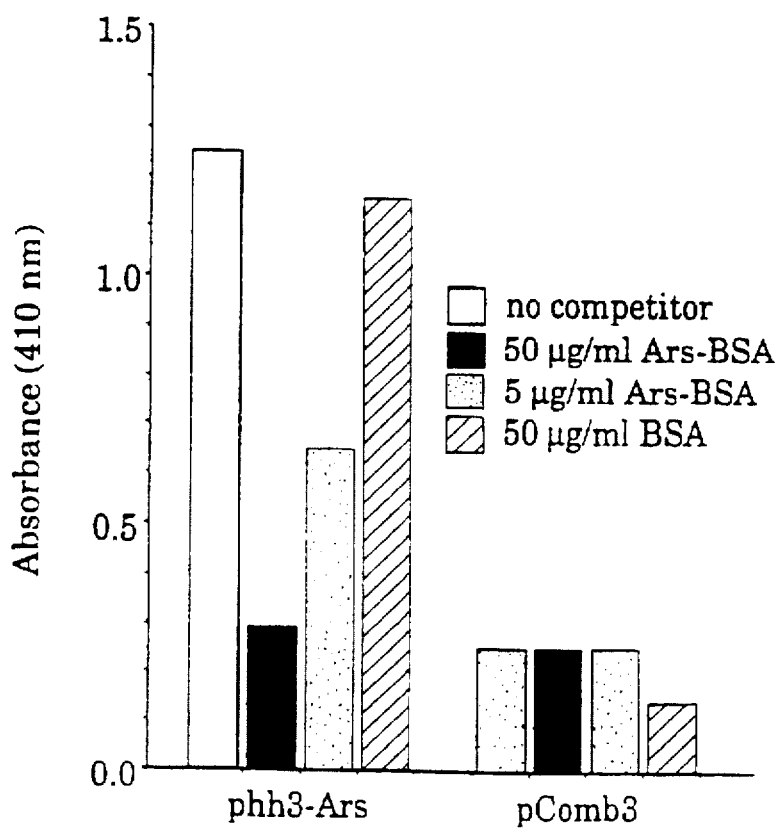

In an additional experiment, a $V_H$-$V_L$ pair derived from a murine antibody to p-azophenylarsonate (Ars) together with the intervening mammalian IPP1 cassette was lifted by PCR from the mammalian expression vector and transferred to phh3mu. The mammalian IPP1 cassette was then exchanged with the prokaryotic IPP1 cassette containing the head-to-head lacZ and tac promoters and the two pelB leader sequences to generate phh3-Ars. As shown in FIG. 9, phage produced from the phh3-Ars vector (FIG. 9A, direct ELISA) bound specifically to a plate coated with Ars-bovine serum albumin (Ars-BSA). Furthermore, the binding to the Ars-BSA coated plate could be specifically inhibited by soluble Ars-BSA, but not by soluble BSA (FIG. 9B).

These results demonstrate that $V_H$-$V_L$ combinations amplified and linked by in-cell PCR, can be transferred successfully to an expression vector. The linked $V_H$-$V_L$ combinations could also easily be first transferred to the phh3 phagemid surface display vector and to the murine or chimeric dual expression vectors (FIG. 4), and that the bidirectional phage display vector can be used successfully for the transfer of a head-to-head linked $V_H$-$V_L$ pair to produce phage particles displaying antigen-binding Fab fragments.

Example 7

In-Cell PCR Amplification and Linking of the $V_H$ and $V_L$ Region Combinations from Untransformed Cells Spleen cells and lymph node cells from immunized mice are prepared after red blood cell lysis, combined, fixed in 10% formaldehyde, permeabilized with 0.1% NP-40, and kept frozen at −80° C. in aliquots of $10^7$ cells until use for in-cell PCR. Additional mice are later immunized with patient-derived Percoll isolated OC2 cells from the frozen aliquots. An aliquot of fixed/permeabilized spleen cells plus lymph node cells derived from the OC2 immune mice is subjected to cDNA synthesis and PCR amplification and linking, but with pools of primers to ensure amplification of all or most V region genes, and with nested primers. The primers used for these reactions are designed to amplify the entire immunoglobulin repertoire, including antibodies to protein epitopes, carbohydrate epitopes and lipid epitopes.

For cDNA synthesis of $V_H$ regions, a pool of primers (1A-CH1 (SEQ ID NO: 1), complementary to the beginning of the CH1 domains of each of the mouse serum isotypes is used (FIG. 5). The pool consists of seven 1A-CH1 primers: 1A-CH1-γ1, 1A-CH1-γ2a, 1A-CH1-γ2b, 1A-CH1-γ3, 1A-CH1-μ, 1A-CHI-ε, and 1A-CHI-α. For cDNA synthesis of $V_L$ regions, a pool of primers (3A-CL (SEQ ID NO: 1)), complementary to the beginning of the Cκ and Cλ domains is used. The four 3A-CL primers are: 3A-CL-κ, 3A-CL-λ1, 3A-CL-λ2, and 3A-CL-λ3.

The same primer pools (1A-CH1 (SEQ ID NO: 2) and 3A-CL (SEQ ID NO: 1)) along with linking primers are used for the first PCR. The linking primers for the $V_H$ regions (2H, sense) are complementary to the beginning of the $V_H$ sequence including part of the leader sequence, have a Xho I restriction enzyme site corresponding to amino acid positions 5 and 6 of the $V_H$ region, and contain in addition a 30 nucleotide-long tail of random sequence. The nine 2H primers, based on the primers used by A. S. Kang et al. (Methods 2:111–18, 1991) are designated 2H1 through 2H9. The linking primers for the $V_L$ regions (4L, (SEQ ID NO: 3)) are complementary to the beginning of the Vκ or Vλ sequences including part of the leader sequence, have a Sac I site corresponding to amino acids 1 and 2 of the $V_L$ region, and contain in addition a 30 nucleotide-long tail which is the reverse complement of the tail of primer 2H (SEQ ID NO: 4). The 4L primers, which are also based on the primers used by A. S. Kang et al. (Methods 2:111–18, 1991) for Vκ and on E. A. Kabat et al. (*Sequences of Proteins of Immunological Interest*, 5th edition, National Institutes of Health, Bethesda, Md., 1991) for Vκ (there are only two Vκ genes in the mouse) are: 4L-Vκ1 through 4L-Vκ7, 4L-Vλ1 and 4L-Vλ2.

The complementary tails of the 2H (SEQ ID NO: 4) and 4L (SEQ ID NO: 3) primers link the $V_H$ and $V_L$ region amplified fragments by overlap extension PCR (H. A. Erlich, *PCR Technology: Principles and Applications for DNA Amplification*, W. H. Freeman & Co., NY, N.Y., 1992). The XhoI and SacI sites introduced by these primers allow for the subsequent cloning of promoter sequences between $V_H$ and $V_L$ sequences. After washing the cells to remove primers and any PCR products that may have leaked from the cells, a second PCR is set up to further amplify the linked $V_H$-$V_L$ region combinations using nested primers (JH and JL, all anti-sense). These primers were designed for the subsequent cloning of the linked $V_H$-$V_L$ combinations into the phh3mu or the phh3hu phagemid vector (FIG. 3). The JH primers, designated JH1–JH4, are complementary to part of a JH gene (there are four JH genes in the mouse), and contain an additional EcoRI restriction site at their 5' ends. The other pool of primers (JL) are each complementary to part of the Jκ or Jλ gene (there are four functional Jκ and three functional Jλ genes in the mouse), and contain an additional HindIII restriction site at their 5' ends. These primers are: Jκ1, Jκ2, Jκ4, Jκ5, Jλ1, Jλ2 and Jλ3.

The first and second PCR products are tested for the presence of DNA fragments by agarose gel electrophoresis. A 0.8 kb fragment is expected after the second PCR. This band, containing the amplified $V_H$-$V_L$ combinations, is gel-isolated using Geneclean II (Bio101; La Jolla, Calif.).

Example 8

Generation of a Fab Phage-Display Library and Soluble Fab Library from the Linked $V_H$-$V_L$ Combinations The gel-isolated $V_H$-$V_L$ combinations are digested with EcoRI and HindIII and ligated with the EcoRI-HindIII backbone from the phh3 phagemid vector (or phh3hu-like vector) to generate a population of phagemid expression vectors phh3/VH–VL as shown in FIGS. 2D and 10. Bacterial transformation and generation of the phage library is performed as described (C. F. Barbas and R. A. Lerner, Methods 2:119–24, 1991). As these vectors are phagemids, they are propagated by transformation and growth of XLI-Blue *E. coli* in culture medium containing carbenicillin and tetracycline. Colonies containing phagemids are cultured on agar by plating out a culture aliquot. To obtain phage, the bacteria are super-infected with excess helper phage VCSM13, after which, packaged phagemids are obtained which infect XLI-Blue *E. coli*.

The phh3/VH–VL ligation mix is transformed by electroporation into competent XLI-Blue SURE bacteria cells, with a transformation efficiency of $5 \times 10^9$ colony forming units (cfu) per ug DNA (Stratagene; La Jolla, Calif.), and aliquots of the transformed cell culture are withdrawn for plating to determine the library size and the number of original members. A good library generally has at least $10^7$ cfu. After expanding the rest of the bacterial culture, double-stranded phagemid DNA are prepared and digested with SacI and XhoI. The large fragment is ligated with a SacI-XhoI fragment containing the head-to-head bacterial promoters derived from phh3 to generate phh3B/VH–VL (FIG. 10).

phh3B/VH–VL-like vectors are obtained by transformation of the ligation mix into SURE electrocompetent cells. Aliquots are plated to ensure a transformation efficiency of at least $10^7$ total cfu. The rest of the transformed bacteria are super-infected with helper phage VCSM13 at $10^{12}$ plaque forming units (pfu) to produce packaged phagemids displaying Fab fragments. This latter step amplifies the library by increasing the representation of each original member. Plaques are precipitated from the cell supernatant with polyethylene glycol and resuspended in PBS. This is the original library.

Soluble Fab is prepared from the phagemid library by digestion with the SpeI and NheI restriction enzymes to remove the gIII coat protein DNA segment, and religated (FIG. 10). Digestion with SpeI and NheI produces compatible cohesive ends which are ligated. The DNA fragment lacking the gIII coat protein portion is gel-purified, self ligated, and transformed into SURE electrocompetent cells. Library titers are determined by plating aliquots. The library is expected to consist of at least $10^7$ cfu. Expression of Fab in the culture is induced with IPTG (for both the lacZ and tac promoters), and cells are lysed by three freeze/thaw cycles between $-80°$ C. and $37°$ C. to yield Fab-containing lysates.

Example 9

Testing the Reactivity of the Original Fab Phage-Display Library

The Fab phage-display library is tested for reactivity with the OC2 tumor and with normal patient/human tissues by immunohistochemistry. Cryostat sections (4 microns thick) are prepared from the OC2 tumor using both the ovary-derived tumor and from the lymph and node metastasis, and from the myometrium, endometrium, and small intestine samples that had been obtained from the OC2 patient. Acetone-fixed cytospin preparations of the patient's PBL and of PBL from another human are tested as described in *Current Protocols in Immunology* (J. E. Coligan et al. editors, John Wiley & Sons, NY, N.Y., 1992). Other cryostat sections from human tissues, such as liver, kidney, heart, lung, skin, spleen, esophagus, jejunum, are prepared from surgical specimens and/or from autopsies performed 6 to 18 hours after death. Immunohistochemistry on both cryostat and cytospin preparations, are performed, except that sheep anti-M13 followed by biotinylated donkey anti-sheep antibodies (5 Prime→3 Prime; Boulder, Colo.) are used as before using avidin-peroxidase to detect bound Fab (M13) phage particles. Alternatively, slides are treated with soluble Fab prepared from the Fab phage display library, followed by biotinylated rabbit anti-mouse kappa before addition of avidin-peroxidase. At this stage, libraries are reactive with the tumor cells as well as with normal cells.

Example 10

Selection of the Fab Phage-Display Library for Reactivity with the OC2 Tumor Cells When the $V_H$–$V_L$ combinations are amplified from mice immune to the OC2 tumor, antibodies that were not directed against the tumor cells or any other human tissue will also be represented. To eliminate those irrelevant antibodies from the library as well as over represented anti-tumor antibodies, the Fab phage-display library is selected for reactivity with Percoll gradient-isolated OC2 tumor cells. Intact, unfixed tumor cells are used to preserve the integrity of the antigenic determinants on the cell membranes.

A 100 ul aliquot of the library containing $10^{11}$ cfu is rocked with $10^7$ washed OC2 cells for 3 hours at room temperature. The cells are pelleted by centrifugation, the supernatant removed, and the cells washed 3 times with PBS to remove unbound phage. Bound phage are eluted from the cells with 0.1M glycine/HCl pH 2.2 containing 1 mg/ml BSA. After 5 minutes, the cell suspension is neutralized with 6 ul of 2M Trizma base and diluted 1:10 with SOC medium. This treatment does not result in lysis of mammalian cells. The vast majority remains intact during the procedure, but some swelling of the cells may be observed. The cells are pelleted by centrifugation, and the supernatant containing the eluted phage used to infect *E. coli* XLI-Blue cells. Aliquots are removed from the transformed cell cultures for plating to determine the number of packaged phagemids that were eluted from the plate. The cultures are infected with helper phage VCSM13 to generate more packaged phagemids. These are rocked with a limiting number of OC2 tumor cells—the number predetermined to be limiting from the retitering of unbound phage particles. Amplification of the eluted phage and further binding to limiting numbers of OC2 cells followed by elution, is repeated three or four times to ensure the tumor-specificity of the selected library. This selected library is tested for reactivity to the OC2 tumor and to normal tissue by immunohistochemistry. It shows a stronger reactivity, but with a similar pattern to that observed for the original library.

Example 11

Absorption of the Tumor-Selected Library with Normal Human/Patient Tissues and PBL The tumor-selected library shows strong cross-reactivity with normal human tissue. The bulk of this cross-reactivity could be absorbed with normal tissue derived from any human source, because the vast majority of human antigens are identical when different individuals are compared (*Molecular Biology of the Cell*, B. Alberts et al. editors, Garland Publishing, Inc., NY, N.Y., 1989). However, the histocompatibility antigens differ among individuals due to polymorphic determinants. While reactivities against the nonpolymorphic determinants of histocompatibility antigens can be absorbed by tissue from any human, tissue derived from the patient is needed to absorb any Fab-phage that react with polymorphic determinants of these antigens. Peripheral blood leukocytes are particularly well suited for this purpose because they collectively express all histocompatibility antigens, including MHC class I antigens, found on all nucleated cells in the body, and the MHC class II antigens found mostly on B cells, monocytes, and dendritic cells.

The Fab phage-display library is absorbed first with normal human PBL, then with a mixture of solid tissue preparations derived from humans in general and from the OC2 patient in particular. Last, the library is absorbed with PBLs from the OC2 patient. After each absorption, the library is reamplified and tested for reactivity against the OC2 tumor and against normal human/patient tissues and PBLs by immunohistochemistry using cryostat sections and cytospin preparations. Re-absorptions with new preparations of the solid tissues or PBLs followed by re-amplifications of the library are continued until the absorbed library reacts with the OC2 tumor much more strongly than with any normal human/patient cells or tissues tested.

For absorption with normal human PBL, freshly prepared whole cells are used. An aliquot of the tumor-selected Fab phage-display library is rocked at room temperature for 3 hours with $1 \times 10^8$ PBLs. Excess cells are removed to ensure that most reactive phage particles were removed.

Membranes are used for absorption with solid tissues. A membrane fraction was already prepared from the myometrium sample obtained from the OC2 patient, and was kept frozen at $-80°$ C. The endometrium and small intestine samples from the OC2 patient, which had been snap-frozen in liquid nitrogen and stored at $-80°$ C., was processed in the same way to prepare membranes. Furthermore, other samples of normal human tissue are obtained from surgical specimens and from autopsies, and membrane fractions prepared and stored in aliquots containing 10% glycerol at $-80°$ C. After thawing, approximately equal membrane aliquots from all the tissues are combined and rocked at room temperature for 3 hours with an aliquot of the human PBL-absorbed Fab phage-display library. The supernatant containing the unabsorbed phage is recovered after pelleting the membranes at $150.000 \times g$.

Final absorption of the Fab phage-display library with PBL from the OC2 patient is accomplished as described for the normal human PBL above, except that only $5 \times 10^6$ cells are used per absorption due to limited supply. Because the library would already be absorbed with normal tissue such as endometrium, myometrium, and small intestine derived from the OC2 patient, and the MHC class I-specific/patient specific Fab phage will already be drastically reduced, the absorption with the patient's PBL is intended to reduce only the MHC class II-specific, patient-specific Fab phage.

Example 12

Assessment of Library Complexity

The optimal (absorbed) library targets many different epitopes (antigenic determinants). Although the tumor cells used for immunization of mice present many epitopes to the immune system, a few are likely to be immunodominant such that antibodies to them will be over represented in the original library. Antibodies to other epitopes will, therefore, be under represented in the original library. Although this would be a major concern with a conventional polyclonal antiserum, the Fab phage-display library approach circumvents this problem. The binding of the library to limiting concentrations of OC2 tumor cells, followed by re-amplification of the bound Fab phage particles, increases the representation of the less immunogenic epitopes. The subsequent absorption of the tumor selected library with normal tissues and PBL reduces drastically the representation of some epitopes in the Fab phage-display library.

An assessment of the number of different epitopes targeted by the tumor-selected/normal tissue absorbed library is obtained by cloning some of the members of the library. Aliquots of XLI-Blue *E. coli* infected with the absorbed Fab phage-display library are plated and individual colonies picked. The double-stranded phagemid vectors are isolated and their V region nucleotide sequence determined. The sequences are analyzed by the BLAST homology search program (S. F. Atltschul et al., J. Mol. Biol. 215:403–10, 1990) available through the Molecular Biology Computer Research Resource, to determine V region subgroup, D gene and J gene usage. This analysis affords a first measure of the library complexity because it indicated whether the clones analyzed are derived from many or very few original B cell clones.

As a second measure of complexity, the ability of the Fab fragments from different clones to cross-compete for binding to the OC2 tumor cells is determined by ELISA using plates coated with OC2 membrane preparations and/or by immuno-histo chemistry. Soluble Fab fragments from different clones compete with the binding of phage-bound Fab fragments from one of the clones where binding of phage is detected with sheep anti-M13 antibodies followed by biotinylated donkey anti-sheep and avidin-peroxidase. If two clones do not cross compete, it is assumed that they are directed to different epitopes. Based on the number of cross-competing clones in a given set of clones, and the number of cfu in the library, the complexity of the library is estimated. This kind of analysis only gives an indication of the number of epitopes or antigenic determinants that are being targeted by the library. It will not disclose how many different antigens are targeted. However, an estimate may be obtained by reacting the library with cellular components separated by 2-dimensional electrophoresis.

Example 13

Generation of an Anti-Tumor Mouse $IgG_{2a}$ Libraries

To determine which of the murine IgG isotypes is most effective at mediating effector functions to eliminate the CD4+ cells, chimeric antibodies were tested for their ability to mediate in vitro complement-dependent cytotoxicity, in vivo cell depletion, and prolongation of allogeneic skin graft survival and suppression of allo-antibody production. Overall, the most effective mouse isotype in these assays was found to be $IgG_{2a}$. Others have also shown $IgG_{2a}$ to be the best mouse isotype in Fc-mediated effector functions. The human $IgG_1$ isotype, which is probably the most analogous isotype to mouse $IgG_{2a}$, has been shown to be one of the two best human isotypes at Fc-mediated effector functions (J. L. Dangl et al., EMBO J. 7:1989–94, 1988).

H and L variable region combinations are expressed from the phagemid library as murine $IgG_{2a}$ antibodies. Before transfer of the linked $V_H$-$V_L$ combinations to the murine $IgG_{2a}$ dual vector (FIG. 4a), the SacI-XhoI DNA fragment containing the head-to-head bacterial promoters and leader sequences in the phagemid vector phh3B/VH–VL (FIG. 10a) is substituted with a SacI-XhoI DNA fragment containing murine H and L promoters and leader sequences in head-to-head transcriptional orientations to generate phh3M/VH–VL (FIG. 10b). The linked $V_H$–$V_L$ combinations including the mammalian promoters are lifted out of the phh3M/VH–VL vector by PCR amplification using 3L and 1H primer pools (FIG. 3).

The 1H primer pool (anti-sense) is complementary to the very beginning of the IgGγ$_{2b}$ CH1 domain and to part of a JH gene (four primers, one for each of the murine JH genes). In addition, this pool of primers contains a HindIII restriction site and a splice site and eliminates the pre-existing EcoRI site of the phh3B/VH–VL vector (FIG. 10a). The 3L primer (SEQ ID NO: 5) is complementary to the very beginning of the Cκ domain and to part of the JL gene (7 primers, for the 4 functional Jκ genes and 3 functional Jλ genes). In additional this pool of primers contains an EcoRI restriction site and a splice site and eliminates the pre-existing HindIII site of the phh3B/VH–VL vector (FIG. 10a).

Figure 4A:
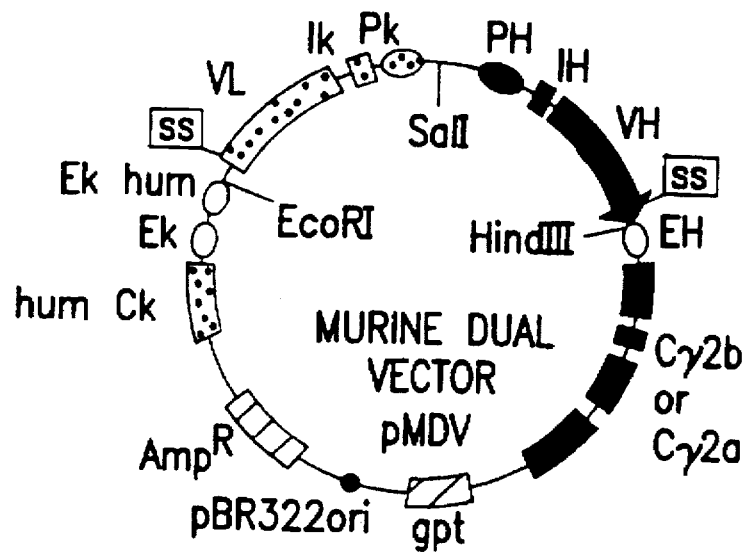
FIG. 4. Schematic diagram of (a) a murine dual vector, pMDV, (b) a chimeric dual vector, pCDV; wherein: P=promoter; E=enhancer; l=leader sequence; ss=splice site; hum=human; and (c) the bulk transfer of variable region sequences between bacterial and mammalian vectors. The amino acids AQVKL (SEQ ID NO: 11) are contributed by the vector.
Figure 4B:
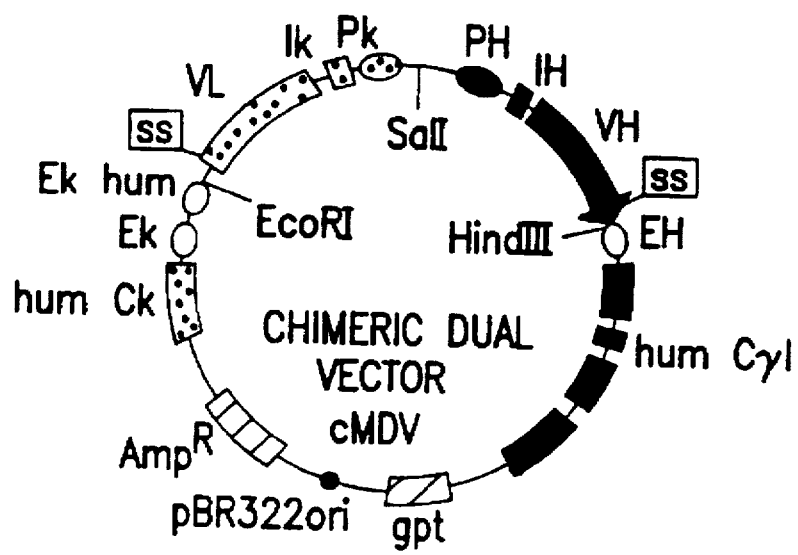
Figure 4C:
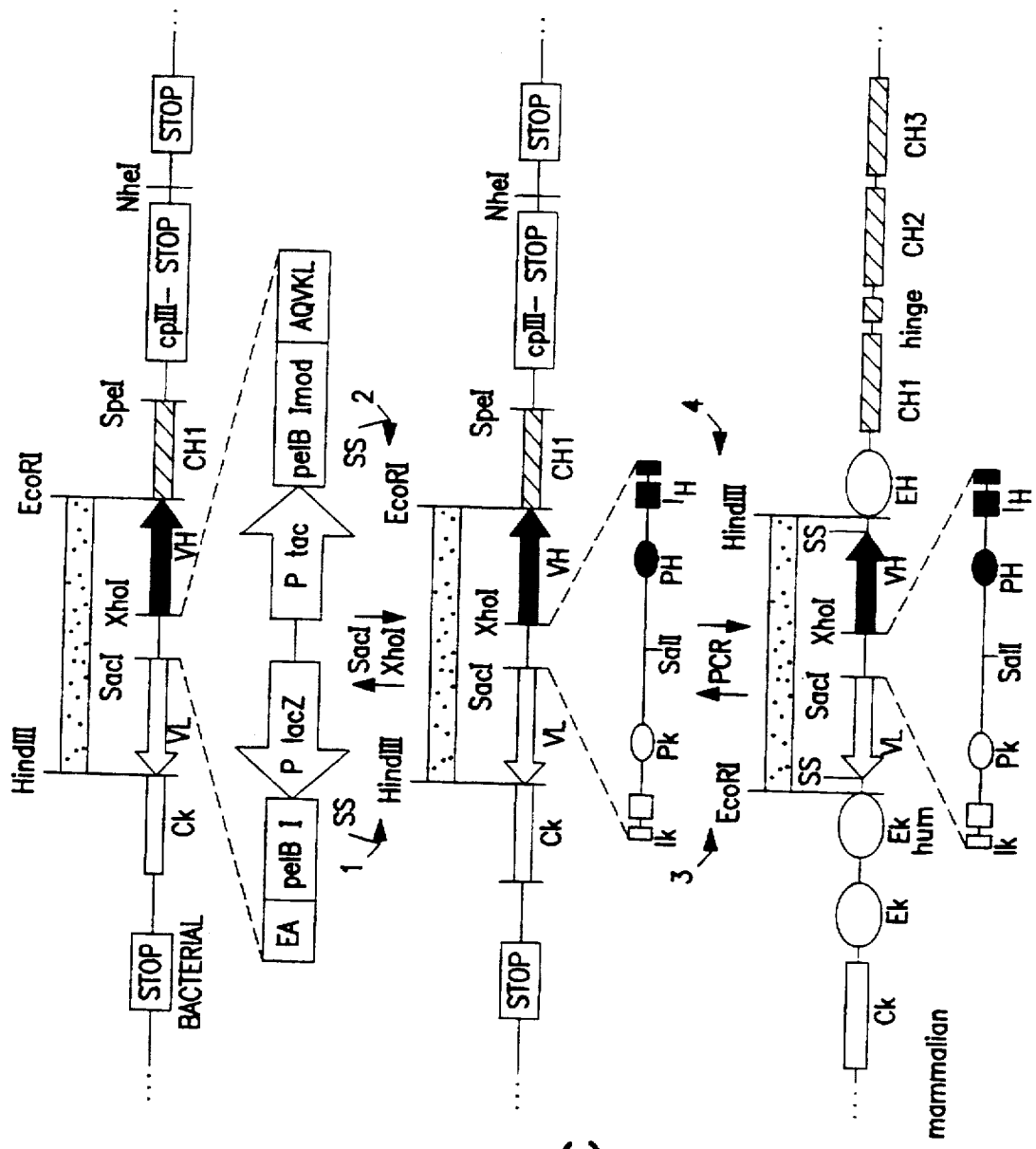

The PCR-amplified DNA fragments are gel-isolated, digested with EcoRI and HindIII, and ligated with the EcoRI-HindIII backbone of the murine IgG$_{2a}$ dual vector (FIG. 4a). The ligation mix is transformed into electrocompetent DH101B cells with a transformation frequency of greater than $10^{10}$ per ug DNA (Gibco/BRL; Grand Island, N.Y.) to generate an IgG$_{2a}$ expression library (IgG$_{2a}$/lib vector). To preserve the complexity of the library during these manipulations, high efficiency transformation bacterial cells and high efficiency transfection mammalian cells are used.

Example 14

Expression of the Mouse IgG$_{2a}$ Library in Hybridoma Cells, Purification of Antibodies, and Assessment of Library Complexity After linearization by restriction enzyme digest at the unique SalI site, the IgG$_{2a}$/lib vector is transfected into the null hybridoma cell line Sp2/0-Ag14 by electroporation, except that 1 ml aliquots containing $2 \times 10^7$ cells each is used per cuvette. Transfectants are recovered in selective medium containing xanthine and mycophenolic acid. The frequency of transfection of the Sp2/0-Ag14 cell line is about 1 in $10^4$ cells, and about 50% of the transfectomas produce significant amounts of immunoglobulin as assessed by Western blot analysis.

For library transfection, $5 \times 10^8$ Sp2/0-Ag14 cells are used and a total of 500–1,000 ug of IgG$_{2a}$ library vector DNA, with the expectation of obtaining a library of about 25,000 clones. The transfected cells are grown for 20 hours after which selective medium containing xanthine and mycophenolic acid is added. Aliquots are removed and plated in selective medium in soft agarose to titer the library. The rest are grown in 4-liter roller bottles in selective medium to allow time for all but the stably transfected cells to die and to achieve a cell density of $2 \times 10^6$ cells/ml.

Antibodies are purified from the culture supernatant on Protein A or Protein G Sepharose (Pharmacia Biotech; Piscataway, N.J.), and purity tested by polyacrylamide gel electrophoresis (PAGE). Based on previous experience with these kinds of transfectants, recovery is expected to be 5–10 ug of IgG per ml of culture supernatant, so it was anticipated obtaining 60 mg of IgG$_{2a}$ library antibodies from 8 liters of culture supernatant.

Although there is no estimate of the complexity of the absorbed Fab phage-display library, it has to be less than $10^7$, the size of the original (unabsorbed) Fab phage-display library. Using a mammalian library 400 times smaller than the original Fab phage-display library (25,000), it is possible, that not all unique members of the absorbed Fab phage-display library will be represented in the mouse IgG$_{2a}$ library. This is not likely because a very high percentage of the library members is eliminated during the absorption with normal human/patient tissues and PBL. Furthermore, the original Fab phage display library of $10^7$ members contains multiple members derived from the same B cell clone, therefore, lowering its actual complexity. In addition, because stable transfection by electroporation results in the integration of several copies of the transfected vector per cell, the size of the mammalian library is likely to be higher than 25,000. Nevertheless, there is a non-zero chance that the mammalian libraries will be less complex than the Fab phage-display library from which they are derived. However, the complexity of the mammalian libraries could not be realistically increased more than half an order of magnitude, before the magnitude of the transfection experiment makes it technically unfeasible.

Due to the above considerations, and more importantly, because individual hybridoma cell transfectants within a population tend to grow at different rates, produce different amounts of immunoglobulin and, sometimes, loose immunoglobulin production, the mammalian IgG libraries are not further propagated by amplifying from a small cell aliquot. Rather, the libraries are generated de novo from the absorbed Fab phage-display library. Initial expansion of the mammalian library for possible future clinical applications will be of a larger scale.

After the expansion of the mammalian libraries, an assessment of their complexity is obtained from the nucleotide sequence of the expressed V region genes. In-cell cDNA synthesis and linking of expressed H and L chain V region genes followed by PCR amplification, is carried out. Linked $V_H$–$V_L$ combinations are then transferred to phh3 the nucleotide sequences of 30 to 40 phagemid clones determined.

Example 15

Effect of the Mouse IgG$_{2a}$ Library on the Growth of the OC2 Tumor in Nude Mice The ability of antibodies with murine C regions to mediate effector functions in a mouse, leading to the elimination of target cells of a particular human tumor, is indicative of the ability of those same antibodies, if provided with human C regions, to mediate effector functions in a human, leading to the elimination of target cells of that tumor. Therefore, the nude mouse is used as a model to test the potential of the anti-tumor library to eliminate tumor target cells in vivo. BALB/c nude mice are injected with 0.25 ml of OC2 tumor pieces or with $10^7$ OC2 tumor cells, both s.c. and i.p. Intravenous injection of tumor cell suspensions are also used when growth of the OC2 tumor is demonstrable in any organ, for example, the spleen or the ovary, following such injections. The mice are injected simultaneously or subsequently with the IgG$_{2a}$ antibody library, or with an equivalent amount of mouse IgG$_{2a}$ for the control group. The effect of antibody treatment is determined by visual and tactile inspection for the development of a subcutaneous tumor. Its dimensions are measured at various times post antibody treatment compared to the control group. Mice injected with tumor intraperitoneally are sacrificed at a time predetermined from examination of control mice to yield a visible tumor in the peritoneal cavity, approximately 3-5 weeks, and checked for tumor growth. All mice including any injected i.v. with tumor cell suspensions are examined, after sacrifice, for metastasis and for tumor necrosis.

Growth of the subcutaneous tumors may be more difficult to inhibit than the growth of the intraperitoneal tumors or tumors at other sites, because the latter may be more accessible to antibodies and effector cells. Both s.c. and i.p. tumors are tested because if s.c. tumors are more difficult to inhibit, their inhibition constitutes an added measure of the potency of the antibody library.

One hundred ug of $IgG_{2a}$ anti-tumor antibody library are administered by i.p. injection 3 days after injection of the tumor pieces. To optimize the process, depending on results, antibody is injected at later or earlier times. Again, depending on results, different doses of $IgG_{2a}$ antibody library, higher or lower than 100 ug per mouse, with repeated injections are administered and with an i.v. route of injection. Different doses of tumor pieces and of OC2 tumor cells may also be administered. At first, only two mice are used for each experimental protocol and three mice for the control (non-specific mouse $IgG_{2a}$). Then, if effective protocols are tested on a group of 5 mice with 5 mice in the control group.

Example 16

Generation of a Chimeric Mouse/Human $IgG_1$ Library and Effect of the Chimeric Mouse/Human $IgG_1$ Library on the Growth of the OC2 Tumor in HU-PBL-SCID Mice A portion of the EcoRI-HindIII DNA fragments preparation, containing the linked $V_H$-$V_L$ combinations including the mammalian promoters and splice sites, is ligated with the EcoRI-HindIII backbone of the chimeric $IgG_1$ dual vector (FIG. 4b) and transformed into DH101B electrocompetent cells to generate a chimeric mouse/human $IgG_1$ expression library. The ability of the chimeric mouse/human $IgG_1$ library to affect the growth of the OC2 tumor is tested in both nude and SCID mice, without and with reconstitution of the SCID mice with human PBL. Human Fc regions have been shown to bind to murine Fc receptors and, therefore, it is possible that the chimeric $IgG_1$ library will inhibit the growth of the OC2 tumor. Both subcutaneous and intraperitoneal tumor growth are tested.

The ability of the chimeric $IgG_1$ antibody library to inhibit the growth of the OC2 tumor in HU-PBL-SCID mice is tested to determine if the human effector cells confer an added advantage. To generate HU-PBL-SCID mice, SCID mice are transplanted intraperitoneally with $2-5 \times 10^7$ adult PBLs separated from whole blood by Ficoll-Paque density gradient centrifugation at the same time as the first injection of the chimeric $IgG_1$ antibody library. The majority of the human PBL remains in the peritoneal cavity and show up in the spleen and blood (as 1-10% of total cells after red blood cell lysis) only 3 to 6 weeks after reconstitution and therefore, testing is only for inhibition of intraperitoneal tumor growth. Complications due to the appearance of Epstein-Barr Virus (EBV)-induced lymphomas in mice reconstituted with PBL from some EBV-seropositive donors are eliminated by terminating EBV positive samples and/or tumors. The time of appearance of these lymphomas varies between 6 and 20 weeks after reconstitution, but is reproducible for a given EBV-seropositive donor. PBLs from some EBV positive donors never gives rise to lymphomas. PBLs from a few donors are pretested and only donors whose PBL do not lead to early development of lymphomas in the reconstituted mice are used. Furthermore, a control group not injected with the OC2 tumor is included in the experiments. The strategy for the doses of antibody, and order and schedule of injection of the antibody library and the OC2 tumor is the same as described for the mouse $IgG_{2a}$ library.

Other embodiments and uses of the invention will be apparent to those skilled in the art from consideration of the specification and practice of the invention disclosed herein. It is intended that the specification and examples be considered exemplary only, with the true scope and spirit of the invention being indicated by the following claims.

I claim:

1. A method for preparing a first library of expression vectors comprising paired nucleic acid fragments, said paired nucleic acid fragments being suitable for transfer to prepare a second library of different expression vectors, comprising the steps of:

(a) obtaining a plurality of nucleic acid fragments wherein each nucleic acid fragment encodes a variable region or part thereof of a protein which contains said variable region;

(b) producing a plurality of nucleic acid segments, wherein each segment comprises a pair of different nucleic acid fragments selected from said plurality of nucleic acid fragments and linked in opposite and divergent transcriptional orientations;

(c) cloning said plurality of nucleic acid segments into first circular vectors to produce a library of vector molecules;

(d) inserting a first cassette between the two nucleic acid fragments of each nucleic acid segment to produce a nucleic acid segment comprising said first cassette in a first library of expression vector molecules, wherein said first cassette contains at least one promoter element permitting expression of said nucleic acid fragments in a first host cell;

(e) introducing said first library of expression vector molecules into the first host cells under conditions and time sufficient to express a first library of polypeptides, wherein each of the polypeptides contains a sequence encoded by one of said pairs of linked nucleic acid fragments; and (f) isolating said first library of expression vector molecules from said first host cells.

2. The method of claim 1, which further comprises isolating the plurality of segments comprising said first cassette from said first library of expression vectors molecules, and inserting said plurality of segments comprising said first cassette into a plurality of second vectors to produce a second library of expression vector molecules.

3. The method of claim 1, which further comprises exchanging said first cassette from an expression vector of said isolated first library of expression vector molecules with a second cassette, wherein said second cassette contains at least one promoter element permitting expression of said nucleic acid fragments in a second host cell.

4. The method of claim 2, which further comprises exchanging said first cassette from an expression vector of said second library of expression vector molecules with a second cassette, wherein said second cassette contains at least one promoter element permitting expression of said nucleic acid fragments in a second host cell.

5. The method of claim 2, wherein said second library of expression vector molecules is introduced into a plurality of second host cells.

6. The method of claim 4, wherein the second vector is a circular vector.

7. The method of claim 5, wherein said first host cell is a prokaryotic cell and said second host cell is a eukaryotic cell.

8. The method of claim 5, wherein said first host cell is a eukaryotic cell and said second host cell is a second eukaryotic cell.

9. The method of claim 5, wherein said first host cell is a prokaryotic cell and said second host cell is a second prokaryotic cell.

10. The method of claim 5, wherein said first host cell is a eukaryotic cell and said second host cell is a prokaryotic cell.

11. The method of claim 1, wherein said protein is a secreted protein or receptor protein.

12. The method of claim 11, wherein the secreted or receptor protein is selected from the group consisting of an antibody and a T-cell receptor.

13. The method of claim 1, wherein one nucleic acid fragment of each segment of said plurality of nucleic acid segments encodes a heavy chain variable region of an antibody and the other nucleic acid fragment of the segment encodes a light chain variable region of the same antibody.

14. The method of claim 1 wherein said nucleic acid fragments comprise a polyclonal population encoding variable regions or portions thereof of proteins selected from the group consisting of antibodies, T-cell receptors, B-cell receptors, natural killer cell receptors, macrophage receptors and combinations thereof derived from a polyclonal cell population.

15. The method of claim 14, wherein the proteins are selected from antibodies or T-cell receptors.

16. The method of claim 1 wherein the first cassette contains two promoters in opposite transcriptional orientations.

17. The method of claim 3 wherein the second cassette contains two promoters in opposite transcriptional orientations.

18. The method of claim 1, wherein said first cassette further comprises a nucleic acid sequence encoding a leader sequence of a secreted protein or membrane protein, and said nucleic acid sequence encoding said leader sequence is operably linked to a nucleic acid fragment of said pair of nucleic acid fragments.

19. The method of claim 3, wherein said first cassette further comprises a nucleic acid sequence encoding a leader sequence of a secreted protein or membrane protein, and said nucleic acid sequence encoding said leader sequence is operably linked to a nucleic acid fragment of said pair of nucleic acid fragments.

20. The method of claim 1, wherein said first circular vector is a prokaryotic or eukaryotic surface display vector or expression vector.

21. The method of claim 2 wherein said second vector is a circular vector.

22. The method of claim 21, wherein said second circular vector is a prokaryotic or eukaryotic surface display vector or expression vector.

23. The method of claim 1 wherein said polypeptides of step (e) are antibodies.

24. The method of claim 23, wherein said antibodies are chimeric antibodies.

25. The method of claim 24, wherein said chimeric antibodies have mouse variable regions and human constant regions.

26. The method of claim 1, wherein step (f) includes a preliminary screening step to select desired expression vector molecules and thereby reduce the number of expression vector molecules used in preparation of said second library from those used in said first library.

* * * * *